United States Patent
Lee et al.

(10) Patent No.: US 6,461,716 B1
(45) Date of Patent: Oct. 8, 2002

(54) APERTURED WEBS HAVING PERMANENT HYDROPHILICITY AND ABSORBENT ARTICLES USING SUCH WEBS

(75) Inventors: Yann-Per Lee, Fairfield; Hugh Joseph O'Donnell, Cincinnati; Andrew Julian Wnuk, Wyoming; Todd Leon Mansfield, Cincinnati, all of OH (US); Gary Dean LaVon, Oberursel (DE); Fernando Benvegnu, Maineville, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/344,161

(22) Filed: Jun. 24, 1999

(51) Int. Cl.$^7$ ................................................ B32B 3/24
(52) U.S. Cl. ..................... 428/137; 428/132; 428/913; 428/423.1; 428/474.7; 428/476.1; 428/480; 428/483; 428/424.8; 604/378; 604/381; 604/382
(58) Field of Search ................................ 428/137, 913, 428/423.1, 474.7, 424.8, 476.1, 480, 483, 132; 604/378, 381, 382

(56) References Cited

U.S. PATENT DOCUMENTS

| | | | |
|---|---|---|---|
| 4,342,314 A | 8/1982 | Radel et al. | 127/287 |
| 4,463,045 A | 7/1984 | Ahr et al. | 428/131 |
| 4,535,020 A | 8/1985 | Thomas et al. | 428/131 |
| 4,629,643 A | 12/1986 | Curro et al. | 428/131 |
| 4,735,843 A | 4/1988 | Noda | 428/137 |
| 4,950,264 A | 8/1990 | Osborn, III | 604/385.1 |
| 5,192,586 A * | 3/1993 | Mertinooke et al. | 427/210 |
| 5,628,844 A | 5/1997 | Nashino et al. | 156/62.4 |
| H1670 H | 7/1997 | Aziz et al. | 604/367 |
| 5,693,037 A * | 12/1997 | Lee et al. | 604/381 |
| 5,741,566 A * | 4/1998 | Hogstrom et al. | 428/35.2 |
| 5,792,412 A * | 8/1998 | Lee et al. | 264/504 |
| 5,834,092 A * | 11/1998 | Lee et al. | 428/131 |
| 5,951,535 A * | 9/1999 | Fujiwara et al. | 604/384 |
| 6,025,049 A * | 2/2000 | Ouellette et al. | 428/131 |
| 6,303,208 B1 * | 10/2001 | Pelkie | 428/138 |

FOREIGN PATENT DOCUMENTS

| | | |
|---|---|---|
| GB | 2 225 724 A | 6/1990 |
| WO | WO 00/00231 | 1/2000 |
| WO | WO 00/13896 | 3/2000 |

* cited by examiner

*Primary Examiner*—William P. Watkins, III
(74) *Attorney, Agent, or Firm*—Edward J. Milbrada; Caroline Wei-Berk; Ken K. Patel

(57) ABSTRACT

The present invention relates to an apertured web formed from a polymeric film having permanent hydrophilicity which is suitable for use as a topsheet in an absorbent article. One embodiment of the present invention is a multi-layer polymeric film having a first layer, a second layer, and at least one intermediate layer between the first and second layers, where one of the first or second layers is a block copolymer of a polyether and another polymer and the other layer is a hydrophobic layer as defined herein. Methods of producing such webs are also disclosed. The present invention also pertains to absorbent articles which preferably include a topsheet in accordance with the present invention, a backsheet secured to the topsheet, and an absorbent core positioned between the topsheet and the backsheet.

38 Claims, 6 Drawing Sheets

APERTURED WEBS HAVING PERMANENT HYDROPHILICITY AND ABSORBENT ARTICLES USING SUCH WEBS

FIELD OF THE INVENTION

The present invention relates to an apertured web comprising a polymeric film having permanent hydrophilicity which is suitable for use as a topsheet in an absorbent article. The present invention also relates to absorbent articles incorporating a topsheet according to the present invention.

BACKGROUND OF THE INVENTION

It has long been known in the field of disposable absorbent articles that it is extremely desirable to construct absorptive devices, such as disposable diapers, sanitary napkins, incontinent briefs, bandages, wound dressings, and the like, presenting a dry surface feel to the user to improve wearing comfort and to minimize the potential for development of undesirable skin conditions due to the prolonged exposure to moisture absorbed within the article. Accordingly, it is generally desirable to promote rapid fluid transfer in a direction away from the wearer and into a retentive structure, while resisting fluid transfer in the reverse direction.

One viable prior art solution to the aforementioned problem has been to utilize a covering or topsheet on the exposed, wearer-contacting layer which comprises a web of formed, apertured thermoplastic film. Commonly assigned US Patent 4,342,314, issued to Radel et al. on Aug. 3, 1982, the disclosure of which is hereby incorporated herein by reference, discloses a representative formed film of this variety. Such webs utilize capillary fluid transport to conduct fluid away from one surface (wearer-contacting) into and through the web via three-dimensional capillaries formed into the material, and then into the underlying absorbent structure. In order to address consumer concerns with regard to plastic-like appearance and feel, webs of this variety have been developed which include an interconnected structure of fiber-like appearance in the interest of generating a more cloth-like, aesthetically-pleasing appearance. In addition, apertured, formed thermoplastic film webs have been developed which further include microscopic surface texturing (microtexture) and/or microscopic apertures (microapertures) to further enhance the visual and tactile impression of such webs. Representative film webs of this variety are disclosed in commonly assigned U.S. Pat. No. 4,463,045, issued to Ahr et al. on Jul. 31, 1984, and U.S. Pat. No. 4,629,643, issued Dec. 16, 1986 to Curro et al., the disclosures of which are hereby incorporated herein by reference.

Another viable prior art solution has been to utilize a fibrous material as a covering or topsheet on such articles, alone or as an overlay or laminate over other materials. A representative topsheet structure of this variety is disclosed in Statutory Invention Registration H1670 published in the name of Aziz et al. on Jul. 1, 1997, the disclosure of which is hereby incorporated herein by reference. Such fibrous materials may take the form of a woven or nonwoven web of a suitable fiber variety, and may or may not include discretely formed apertures in addition to the inherent porosity of the web itself. Webs of this variety also exhibit capillary fluid transport characteristics via the three-dimensional capillaries formed by inter fiber spaces, likewise conducting fluid away from the wearer-contacting surface and into the underlying absorbent structure. Such webs exhibit an aesthetically-pleasing, cloth-like surface appearance and tactile impression due to the fibrous nature of the surface.

Another prior art solution to increase the rate of fluid transfer away from the wearer has been the addition of a surfactant, or wetting agent, to the web to increase wettability. The surfactant may either be incorporated into the web itself (resin incorporated surfactant (RIS)) in accordance with U.S. Pat. No. 4,535,020, issued in the name of Thomas, et al. on Aug. 13, 1985 and the aforementioned Statutory Invention Registration H1670, or, alternatively, may be applied to the surface of the web by spraying, printing, or other suitable methods such as disclosed in U.S. Pat. No. 4,950,264, issued to Osborn on Aug. 21, 1990.

The art has also used depositions of a low surface energy material on a surface of an apertured web having an underlying polymeric structure with a higher surface energy to provide a surface energy gradient. As described herein, such a surface energy gradient facilitates movement of moisture from the top surface of the web to the back surface. An example of this method is disclosed in commonly assigned U.S. Pat. No. 6,025,049, issued to to Ouelette et al. on Feb. 15, 2000. An exemplary coating material is a hydrophobic silicone resin. While such low surface energy depositions provide desirable fluid handling properties, they are relative expensive and require additional process steps.

While capillary webs of the foregoing varieties are effective in transporting fluid, their effectiveness is limited in that such capillary structures can only move fluid once it reaches the capillary interior. Fluid which wets and remains on wearer contacting surfaces contributes to a "wet" tactile feeling or impression, and to the extent that such fluid may be colored or opaque also contributes to a "stained" visual impression. Surface textures naturally occurring in the material of the web or imparted thereto in formation further increase the likelihood that residual fluid will be trapped or retained on the wearer-contacting surface rather than entering capillary structures for transport away from the surface. Thus, surface topographies which contribute to desirable visual and tactile impressions when dry can also tend to retain residual fluid on the exposed surface and thus reduced desirability under in-use conditions.

Another problem associated with prior art capillary webs is their fluid retention when subjected to pressures associated with their use. The topsheet webs of the prior art do not prevent some of the fluid that has been transported away from the surface from passing back through the topsheet onto the wearer contact surface. As with fluid that remains on the wearer contact surface, fluid that passes back through the topsheet onto the wearer contact surface also contributes to a "wet" tactile feeling or impression, and a "stained" visual impression.

Additionally, the RIS approach has several disadvantages. First, the surfactant is migratable, meaning that it may diffuse away from the topsheet, thus reducing topsheet wettability and possibly contaminating other components of the absorbent article. Second, surfactant may be lost during the forming process, thus potentially leading to foaming of the water system used for forming. Third, surfactant on the surface of the topsheet is normally depleted during use due to surfactant wash-off and migration. Finally, surfactants commonly used in absorbent articles are often complex molecules and mixtures of complex molecules. This results in surfactant having varying migration and therefore the topsheet experiences a surfactant composition that changes over time. The above disadvantages can result in a web having wettability with little durability.

Accordingly, it would be desirable to provide a web with enhanced effectiveness in transporting fluid away from one surface which is initially contacted by a fluid. It would also be desirable to provide a web that better prevents absorbed fluid from passing back out of the absorbent core of the article and onto the wearer contacting surface. Additionally, it would be desirable to provide a topsheet having durable wettability, i.e., permanent hydrophilicity, while avoiding the complexity of the RIS process. It would also be desirable to achieve a surface energy gradient while avoiding the use of hydrophobic coatings or surfactant treatments.

More particularly, it would be desirable to retain pleasing visual and tactile properties of webs having fibrous or otherwise textured surfaces while promoting more rapid and more complete fluid transport away from the wearer-contacting surface and into the interior of an associated absorbent article.

SUMMARY OF THE INVENTION

The present invention pertains to an apertured formed polymeric film web suitable for use as a topsheet on a disposable absorbent article. In one embodiment of the present invention the formed polymeric film web comprises a first layer, a second layer, and at least one intermediate layer between the first and second layers, where one of the first or second layers comprises a hydrophilic composition comprising a block copolymer of a polyether and another polymer, and the other layer comprises a hydrophobic composition as defined herein.

Another embodiment of the present invention is the formed polymeric film web comprises a first layer, a second layer, and at least one intermediate layer between the first and second layers, where both the first and second layers comprise a hydrophilic composition comprising a block copolymer of a polyether and another polymer.

A further embodiment of the present invention, the formed polymeric film web, comprises a dual-layer polymeric film comprising a first layer and a second layer where one of the first or second layers is hydrophilic and comprises a block copolymer of a polyether and another polymer and the other layer comprises a hydrophobic composition as defined herein.

A still further embodiment of the present invention the formed polymeric film web comprises a dual-layer polymeric film comprising a first layer and a second layer where both the first and second layers comprise a hydrophilic composition comprising a block copolymer of a polyether and another polymer.

A still further embodiment of the present invention the formed polymeric film web comprises a monolayer film comprising a hydrophilic layer comprising a block copolymer of a polyether and another polymer.

The polymeric film of the present invention provides many advantages. The use of a block copolymer of a polyether and another polymer as the hydrophilic layer renders the film permanently hydrophilic. The permanent hydrophilicity gives the film durable wettability without the need for surfactant treatment, thus avoiding the problems of the prior art.

The apertured formed film web, comprising a polymeric film in accordance with the present invention, may also be provided with a surface energy gradient, defined herein, which assist in the effective transport of fluid away from the first or wearer-contacting surface. The web essentially retains its visual, tactile, and physical properties of the substrate polymeric film material while achieving the desired surface energy properties.

The present invention also pertains to absorbent articles which preferably include a topsheet formed from the formed film web of the present invention, a backsheet secured to the topsheet, and an absorbent core positioned between the topsheet and the backsheet.

BRIEF DESCRIPTION OF THE DRAWINGS

While the specification concludes with claims particularly pointing out and distinctly claiming the present invention, it is believed that the present invention will be better understood from the following description in conjunction with the accompanying drawings, in which like reference numbers identify like elements, and wherein:

DETAILED DESCRIPTION OF THE PRESENT INVENTION

Definitions

Figure 1:
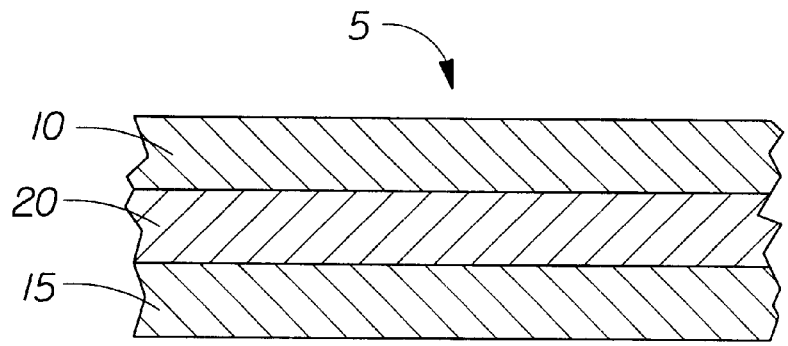
FIG. 1 is a cross-sectional view showing one embodiment of polymeric film of the present invention.

As used herein, the term "hydrophilic" is used to refer to surfaces that are wettable by aqueous fluids (e.g., aqueous body fluids) deposited thereon. Hydrophilicity and wettability are typically defined in terms of water contact angle and the surface tension of the fluids and solid surfaces involved. This is discussed in detail in the American Chemical Society publication entitled *Contact Angle, Wettability and Adhesion*, edited by Robert F. Gould (Copyright 1964), which is hereby incorporated herein by reference. A surface is said to be wetted by a fluid (hydrophilic) when the fluid tends to spread spontaneously across the surface as opposed to forming discrete droplets. Conversely, a surface is considered to be "hydrophobic" if the fluid tends to form discrete droplets and does not spread spontaneously across the surface. As used herein, a "hydrophilic film or layer" generally has a water contact angle less than about 50 degrees. As used herein, a "hydrophobic film or layer" generally has a water contact angle greater than about 50 degrees.

The water contact angle depends on surface inhomogeneities (e.g., chemical and physical properties, such as roughness), contamination, chemical/physical treatment of the solid surface, or composition of the solid surface, as well as contamination of the water. The surface energy of the solid also influences the water contact angle. As the surface energy of the solid decreases, the water contact angle increases. As the surface energy of the solid increases, the water contact angle decreases.

The energy required to separate a liquid from a solid surface (e.g., a film or fiber) is expressed by equation (1):

$$W = G(1 + \cos A) \quad (1)$$

where:
  W is the work of adhesion measured in erg/cm$^2$
  G is the surface tension of the liquid measured in dyne/cm, and
  A is the liquid-solid water contact angle measured in degrees.

With a given liquid, the work of adhesion increases with the cosine of the liquid-solid water contact angle (reaching a maximum where the water contact angle A is zero).

Work of adhesion is one useful tool in understanding and quantifying the surface energy characteristics of a given surface. Another useful method which could be utilized to characterize the surface energy characteristics of a given surface is the parameter labeled "critical surface tension", as discussed in H. W. Fox, E. F. Hare, and W. A. Zisman, J. Colloid Sci. 8, 194 (1953), and in Zisman, W. A., Advan. Chem. Series No. 43. Chapter 1, American Chemical Society (1964), both of which are hereby incorporated herein by reference.

Illustrated below in Table 1 is the inverse relationship between water contact angle and work of adhesion for a particular fluid (e.g., water), whose surface tension is 75 dynes/cm.

TABLE 1

| A (degrees) | cos A | 1 + cos A | W (erg/cm$^2$) |
|---|---|---|---|
| 0 | 1 | 2 | 150 |
| 30 | 0.87 | 1.87 | 140 |
| 60 | 0.5 | 1.50 | 113 |
| 90 | 0 | 1.00 | 75 |
| 120 | −0.5 | 0.5 | 38 |
| 150 | −0.87 | 0.13 | 10 |
| 180 | −1 | 0 | 0 |

As shown in Table 1, as the work of adhesion decreases (i.e. the surface exhibits a lower critical surface tension), the contact angle for water on the surface increases, and hence the fluid tends to "bead up" and have a smaller surface area of contact. The reverse is likewise true with contact angle decreasing with increasing work of adhesion.

As utilized herein, the term "fluid passageway" is intended to encompass enclosed or at least partially enclosed structures or channels which may communicate fluids. The term fluid passageway is thus intended to encompass the terms "aperture", "channel", "capillary", as well as other similar terms.

As used herein, the term "gradient" when applied to differences in surface energy or work of adhesion is intended to describe a change in surface energy or work of adhesion occurring over a measurable distance. The term "discontinuity" is intended to refer to a type of "gradient" or transition, wherein the change in surface energy occurs over an essentially zero distance. Accordingly, as used herein all "discontinuities" fall within the definition of "gradient".

Also, as used herein the terms "capillary" and "capillarity" are used to refer to passageways, apertures, pores, or spaces within a structure which are capable of fluid transport in accordance with the principles of capillarity generally represented by the Laplace equation (2):

$$\Delta p = 2G(\cos A) / R \quad (2)$$

where:
  p is the capillary pressure;
  R is the internal radius of the capillary (capillary radius); and
  G and A are as defined above.

As noted in *Penetration of Fabrics* by Emery I. Valko, found in Chapter III of *Chem. Aftertreat. Text.* (1971), pp. 83–113, which is hereby incorporated herein by reference, for A=90°, the cosine of A is zero and there is no capillary pressure. For A >90°, the cosine of A is negative and the capillary pressure opposes the entry of fluid into the capillary. For A <90° the cosine of A is positive and the capillary pressure permits the entry of fluid into the capillary. Also, R must be sufficiently small for p to have a meaningful value, since as R increases (larger aperture/capillary structure) the capillary pressure decreases.

As utilized herein, the term "incompatible" represents the lack of miscibility between two materials such that each phase substantially retains its original properties. Example properties include glass transition temperature or melting point. Another and more practical characterization of incompatible materials is that the strength of the interface is significantly weaker than the strength of the weakest individual phase (material). Thus, the work of adhesion between the two materials is much lower than the lowest cohesive energy of either material, and the risk of delamination is high.

The term "topsheet" generally refers to the cover layer, in an absorbent article such as a diaper or catamenial pad, that faces the wearer of the absorbent article. The term "wearer-contacting layer or surface" as used herein refers to the surface of a topsheet or other absorbent article component that is nearest the wearer of the article. The term "garment-facing layer or surface" refers to the surface of a topsheet or other absorbent article component that faces away from the wearer when the component is used in an absorbent article.

The term "Z-dimension" refers to the dimension orthogonal to the length and width of the layer, structure or article. The Z-dimension usually corresponds to the thickness of the layer, structure or article.

The terms "fiber-like" or "cloth-like," as utilized herein to describe the appearance of plastic polymeric films, refers generally to any fine scale pattern of embossments or apertures, random or non-random, reticulated or non-reticulated, which can provide an overall appearance and impression of a woven or nonwoven fibrous polymeric structure when viewed by the human eye at a distance of 12inches (30 cm). When describing the elements used to form the polymeric film, the term "fiber-like" is utilized herein to describe the appearance or shape of the elements.

As utilized herein, the term "macroscopically expanded," when used to describe three-dimensional plastic webs, ribbons and films, refers to webs, ribbons and films which have been caused to conform to the surface of a three-dimensional forming structure so that both surfaces thereof exhibit the three-dimensional pattern of said forming structure, said pattern being readily visible to a normal human eye when the perpendicular distance between the viewer's eye and the plane of the web is about 12inches (30 cm).

In general, as utilized herein the term "macroscopic" is used to refer to structural features or elements which are readily visible to a normal human eye when the perpendicular distance between the viewer's eye and the plane of the web is about 12inches. Conversely, the term "microscopic" is utilized to refer to structural features or elements which are not readily visible to a normal human eye when the perpendicular distance between the viewer's eye and the plane of the web is about 12inches (30 cm).

As used herein, the term "absorbent article" refers to devices which absorb and contain body exudates, and, more specifically, refers to devices which are placed against or in proximity to the body of the wearer to absorb and contain the various exudates discharged from the body. The term "disposable" is used herein to describe absorbent articles which are not intended to be laundered or otherwise restored or reused as an absorbent article (i.e., they are intended to be discarded after a single use, and, preferably, to be recycled, composted or otherwise disposed of in an environmentally compatible manner). A "unitary" absorbent article refers to absorbent articles which are formed of separate parts united together to form a coordinated entity so that they do not require separate manipulative parts like a separate holder and pad.

The Polymeric Film of the Present Invention

The polymeric film of the present invention may comprise one of many different configurations depending on the film properties desired. The properties of the polymeric film of the present invention may be manipulated by varying, for example, the number of layers, the chemistry of the layers, i.e., hydrophobic or hydrophilic, and the types of polymers used to form the polymeric layers.

One embodiment of the polymeric film of the present invention is a multi-layer film comprising a first layer, a second layer, and at least one intermediate layer between the first and second layers. Each of the first and second layers may be either a hydrophobic layer or a hydrophilic layer comprising a block copolymer of a polyether and another polymer. If the multi-layer polymeric film includes two adjacent layers that comprise incompatible materials, then the intermediate layer between them preferably is a tie layer, tie layers being defined below.

FIG. 1 is a cross-sectional view of one embodiment of a multi-layer polymeric film of the present invention, generally depicted as 5. This embodiment is a three layer polymeric film comprising a first layer 10, a second layer 15, and an intermediate layer, 20. Preferably, one of the first and second layers is a hydrophobic layer while the other layer is a hydrophilic layer comprising a block copolymer of a polyether and another polymer. In such a case, the intermediate layer 20 is preferably a tie layer that facilitates the bonding of the incompatible hydrophobic and hydrophilic layers. Such tie layers are described in further detail below.

The first and second layers may also both be hydrophilic. If the first and second layers comprise incompatible materials, then the intermediate layer preferably is a tie layer.

Figure 2:
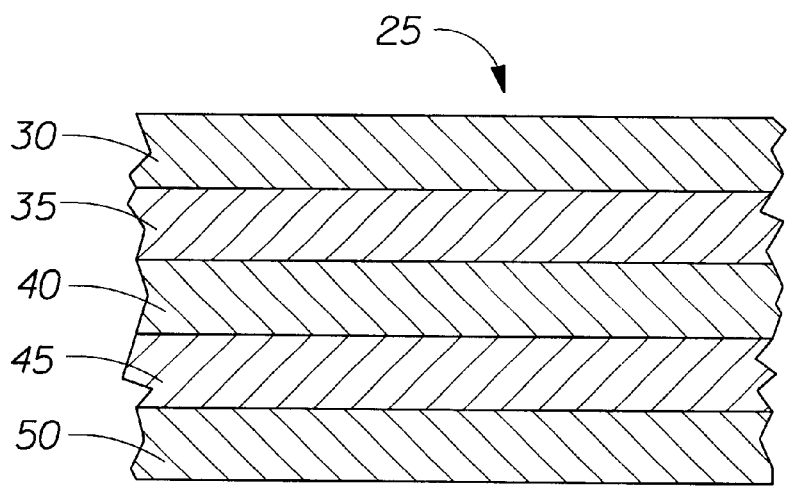
FIG. 2 is a cross-sectional view showing one embodiment of the polymeric film of the present invention.

FIG. 2 is a cross-sectional view of another embodiment of the polymeric film of the present invention, generally depicted as 25. This embodiment is a five layer polymeric film comprising a first layer 30, a second layer 35, a third layer 40, a fourth layer 45, and a fifth layer 50. One of the first and fifth layers is hydrophobic while the other layer is a hydrophilic layer comprising a block copolymer of a polyether and another polymer. Alternatively, as with the three layer film, the first and fifth layers may both be hydrophilic.

Film structures having three or more layers are preferred for purposes of the present invention for several reasons including: 1) such structures provide hydrophilicity at minimal usage of the relatively expensive hydrophilic block copolymers described herein; 2) such structures can compensate for nonoptimal film forming and converting properties of a hydrophilic layer; and 3) such structures can compensate for nonoptimal mechanical properties of a hydrophilic layer. While multi layered structures are preferred, film structures comprising one or two layers are also within the scope of the present invention. Exemplary structures of this type are described below.

Figure 3:
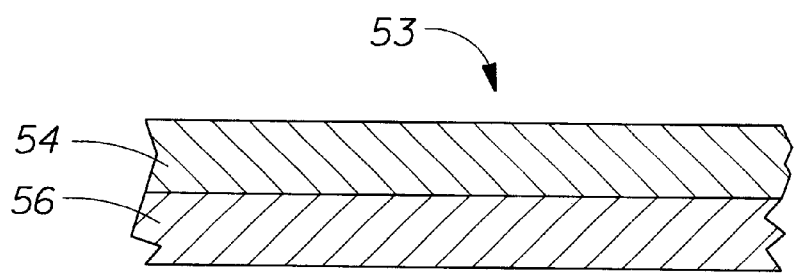
FIG. 3 is a cross-sectional view showing one embodiment of the polymeric film of the present invention.

FIG. 3 is a cross-sectional view of a further embodiment of the polymeric film of the present invention, generally depicted as 53. The film 53 is a dual layer film comprising first layer 54 and second layer 56. In accordance with the present invention, one of the first and second layers may be hydrophilic while the other is hydrophobic. Alternatively, the first and second layers may both be hydrophilic. This alternative structure can have particularly useful properties because, with proper choice of layer composition, hydrophilic layers having different degrees of hydrophilicity can be produced. Such a dual layer film can then be apertured and the lands thereof provided with microscopic depositions of a low surface energy material as described below to provide a topsheet material having desirable fluid handling properties.

Although the foregoing embodiments of the present invention are multi-layer films, the polymeric film of the present invention may comprise a monolayer hydrophilic film as well. An apertured monolayer film that is provided with a surface energy gradient as described below would also have desirable fluid handling properties.

The polymeric film of the present invention may include any number of layers as long as there is a tie layer between any adjacent layers that comprise incompatible materials. In addition, the intermediate layer or layers may comprise any polymeric material as long as there is a tie layer between any adjacent incompatible layers. Any number of intermediate layers may be utilized in forming the polymeric films of the present invention as long as one of the outer layers is a hydrophilic layer comprising a block copolymer of a polyether and another polymer. Depending on the preferred structure, the other outer layer may be either a hydrophilic block copolymer or a hydrophobic polymer as described above.

As described herein below, another aspect of the present invention is a topsheet comprising the polymeric film of the present invention. The material selected for the polymeric film of the present invention, and therefore for the topsheet formed therefrom, is preferably machinable and capable of being formed into a sheet. Since the topsheet is to be used in consumer products which contact the human body, the material utilized in the polymeric film used to form the topsheet is safe and preferably soft for epidermal or other human contact.

Generally, the hydrophilic layer of the present invention comprises a polymer selected from a class of compounds generally described as block copolymers. The blocks are comprised of hydrophobic segments and hydrophilic segments. Generally, the hydrophobic blocks are termed "hard" because the glass transition temperature is typically above room temperature. Contrarily, the hydrophilic blocks are termed "soft" because the glass transition temperature is typically below room temperature. Suitable hard blocks include 1) polyesters such as poly(ethylene terephthalate) and poly(butylene terephthalate); 2) polyamides such as nylon 6 and nylon 66; 3) polyurethanes. Suitable soft blocks include polyethers such as poly(butylene glycol), poly(ethylene glycol), poly(ethylene glycol - co - propylene glycol). Preferably, the hydrophilic layer comprises a segmented block copolymer of the above-identified hard and soft blocks.

Exemplary hydrophilic copolyetheresters comprise a hydrophilic elastomer or a mixture of two or more hydrophilic copolyetherester elastomers having a multiplicity of recurring long-chain ester units and short chain ester units joined through ester linkages, the long-chain ester units being represented by the formula.

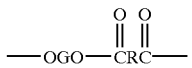

and the short-chain ester units being represented by the formula:

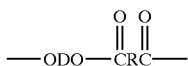

where G is a divalent radical remaining after the removal of terminal hydroxyl groups from a poly(alkylene oxide) glycol having an average molecular weight of about 400–4000; R is a divalent radical remaining after removal of carboxyl groups from a dicarboxylic acid having a molecular weight less than 300; and D is a divalent radical remaining after removal of hydroxyl groups from a diol having a molecular weight less than about 250.

Representative long-chain glycols used to prepare the copolyetheresters that form the hydrophilic material include poly(ethylene oxide) glycol, poly(1,2 and 1,3-propylene oxide) glycol, poly(tetramethylene oxide) glycol, ethylene oxide capped polypropylene oxide glycol, mixtures of poly(ethylene oxide) glycol with other glycols such as ethylene oxide capped poly(propylene oxide) glycols and/or poly(tetramethylene oxide) glycol and their random or block copolymers provided the resulting copolyetherester has an amount of ethylene oxide groups of at least about 25 weight percent. Preferably, the amount of ethylene oxide groups incorporated in the copolyetherester or mixture of two or more copolyetheresters by the poly(alkylene oxide) glycol is from about 25–75 and, more preferably, from about 40 to 68 weight percent based on the total weight of the copolyetherester or mixture of two or more copolyetheresters. The ethylene oxide groups in the copolyetherester that are counted to determine the amount in the polymer are those derived from the poly(alkylene oxide) glycol and not ethylene oxide groups that can be introduced into the copolyetherester by means of low molecular weight diol.

Examples of such compounds can be found in U.S. Pat. No. 4,725,481 issued to Ostapchenko on Feb. 16, 1988, herein incorporated by reference. Such compounds are block copolymers of a polyester and a polyether and are sold by DuPont of Wilmington, Del. under the tradename Hytrel®. A preferred polyetherester of this type of compound is a copolymer of a polyalkylene terephthalate (a polyester derivative polymer) having the following structure:

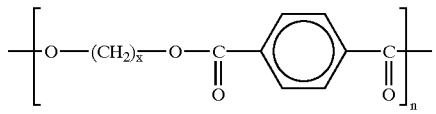

in which x equals 2 or 4, and a long chain polyether glycol having the following structure:

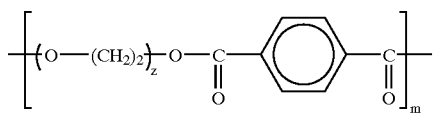

in which z is between about 8 and about 80. Hytrel® is available in a variety of formulations of varying hydrophilicity. Preferred for the present invention are formulations sold under the names Hytrel® HTR 8171 or Hytrel® HTR 8206. Particularly preferred is a blend of equal parts of Hytrel® HTR 8171 or Hytrel® HTR 8206.

Another example of a suitable block copolymer for use as the hydrophilic material is a group of compounds generally comprising block copolymers of a polyether and a polyamide. Each of the polyetheramide copolymers have polyether segments and polyamide segments. Exemplary polyethers are polyetherdiols including polyethylene glycol, polypropylene glycol, polytetramethylene glycol, mixtures of at least two of such polyetherdiols, and their copolymers. Exemplary copolyetherdiols include random and/or block copolymers of ethylene glycol and/or of 1,2 or 1,3 propylene glycol. The molecular weight of these polyethers ranges from about 250 to 10,000 and preferably from 400 to 4,000. The polyetheramide preferably contains between 40 wt. % and 80 wt % polyether and more preferably between 50 wt % and 70 wt %. These segments may be prepared by reacting a dicarboxylic polyamide with a polyoxyalkylene glycol at sufficiently elevated temperature and under sufficiently high vacuum in the presence of a suitable catalyst. Polymers of this type are discussed more fully in U.S. Pat. No. 4,331,786, 4,839,441, 4,839,441, 4,273,898, 5,166,309, and 5,213,891. The disclosure of each being incorporated herein by reference.

Such materials are commercially available from Elf Atochem North America, Inc. of Philadelphia, Pa. under the tradename Pebax®.

Still another example of a suitable block copolymer for use as the hydrophilic material is a group of compounds generally comprising block copolymers of a polyether and a polyurethane as are available from BF Goodrich High Performance Materials of Cleveland, Ohio under the tradename Estane®.

While the chemistry of the block copolymer of a polyether and another polymer may vary, the primary measure of polymer acceptability is the water contact angle. The hydrophilic block copolymer layer of the polymeric film of the present invention preferably has a water contact angle less than about 50 degrees, more preferably less than about 40 degrees, and most preferably less than about 30 degrees.

It is preferred that the hydrophobic layer comprise a soft resin with a modulus less than 1,000 MPa, preferably less than 700 MPa, be used. Suitable test methods for measuring the modulus of a polymer include ASTM D882 or D632. Many resins may meet this criterion by using copolymers, tacticity in homopolymers, blends with softer materials, or additives such as plasticizers. The hydrophobic layer is typically comprised of a polyolefin resin such as polyethylene. A preferred polyethylene is available from Tredegar Film Products of Richmond, Va. under the code X-8318. Other polyolefin resins such as polypropylene, ethylene vinyl acetate, and ethylene methyl acrylate may be used. Other thermoplastic resins such as polyester, polyamides, and polyvinyl chloride may be used if: (1) the water contact angle of the resin falls within the range of acceptable values set forth herein, (2) suitable tie layer materials exist, and (3) the resins are amenable to thermoplastic processing to form the multi-layer films of the present invention. For example, an aliphatic polyester can be used as the hydrophobic layer. Films from these materials can easily be fabricated into formed films. Such resins generally have the added benefit of not requiring a tie layer when used with hydrophilic resins such as the polyetherester resins described above. In certain embodiments, aliphatic polyesters are also biodegradable providing additional utility. Another example of a suitable polyester-type resin that is suitable for the hydrophobic layer of the present invention is a hydrophobic block copolymer of a polyester and a polyether to provide a water contact angle that is about 60° that is available from DuPont as Hytrel® HTR 5556.

The hydrophobic layer of the polymeric film of the present invention preferably has a water contact angle greater than about 50 degrees, more preferably greater than about 80 degrees.

If incompatible polymeric layers are to be adjacent in a multi-layer polymeric film structure, a tie layer is preferably positioned between them. The purpose of the tie layer is to provide a transition and adequate adhesion between incompatible materials. An adhesive or tie layer is typically used between layers of thermoplastic resins that exhibit delamination when stretched, distorted, or deformed. The delamination may be either microscopic separation or macroscopic separation. In either event, the performance of the film may be compromised. Consequently, a tie layer that exhibits adequate adhesion between the layers should be used.

A tie layer would generally be useful between incompatible materials such as when a copoly(ester-ether) is not adjacent to another copoly(ester-ether). For instance, when a polyolefin and a copoly(ester-ether) are the adjacent layers, a tie layer would generally be useful.

The tie layer is chosen according to the nature of the adjacent materials. It will have a backbone that is compatible with and is preferably identical to one material (e.g. non-polar and hydrophobic layer) and a reactive group which is compatible or interacts with the second material (e.g. polar and hydrophilic layer).

Suitable backbones for the tie layer include polyethylene (low density—LDPE, linear low density—LLDPE, high density—HDPE, and very low density—VLDPE) and polypropylene.

The reactive group may be a grafting monomer that is grafted to this backbone, and is or contains at least one alpha- or beta- ethylenically unsaturated carboxylic acid or anhydrides, or a derivative thereof. Examples of such carboxylic acids and anhydrides, which maybe mono-, di-, or polycarboxylic acids, are acrylic acid, methacrylic acid, maleic acid, fumaric acid, itaconic acid, crotonic acid, itaconic anhydride, maleic anhydride, and substituted malic anhydride, e.g. dimethyl maleic anhydride. Examples of derivatives of the unsaturated acids are salts, amides, imides and esters e.g. mono- and disodium maleate, acrylamide, maleimide, and diethyl fumarate.

A particularly preferred tie layer is a low molecular weight polymer of ethylene with about 0.1 to about 30 weight percent of one or more unsaturated monomers which can be copolymerized with ethylene, e.g., maleic acid, fumaric acid, acrylic acid, methacrylic acid, vinyl acetate, acrylonitrile, methacrylonitrile, butadiene, carbon monoxide, etc. Preferred are acrylic esters, maleic anhydride, vinyl acetate, and methyacrylic acid. Anhydrides are particularly preferred as grafting monomers with maleic anhydride being most preferred.

An exemplary class of materials suitable for use as a tie layer is a class of materials known as anhydride modified ethylene vinyl acetate sold by DuPont under the tradename Bynel®. A preferred anhydride modified ethylene vinyl acetate formulation is sold by DuPont under the tradename Bynel® 3860. Another material suitable for use as a tie layer is an anhydride modified ethylene methyl acrylate also sold by DuPont under the tradename Bynel®. A preferred anhydride modified ethylene methyl acrylate is sold by DuPont under the tradename Bynel® 2169. Maleic anhydride graft polyolefin polymers suitable for use as tie layers are also available from Elf Atochem North America, Functional Polymers Division, of Philadelphia, Pa. as Orevac™.

Alternatively, a polymer suitable for use as a tie layer material can be incorporated into the composition of one or more of the layers of the polymeric film of the present invention. By such incorporation, the properties of the various layers are modified so as to improve their compatibility and reduce the risk of delamination.

Other intermediate layers besides tie layers may be used in the multi-layer polymeric film of the present invention. For example, a layer of a polyolefin resin could be used between two outer layers of a hydrophilic resin, such as those discussed above, to provide additional mechanical strength to the extruded web. Any number of intermediate layers may be used. Examples of suitable thermoplastic materials for use in forming intermediate layers include polyethylene resins such as low density polyethylene (LDPE), linear low density polyethylene (LLDPE), ethylene vinyl acetate (EVA), ethylene methyl acrylate (EMA), polypropylene, and poly(vinyl chloride). Preferred polymeric layers of this type have mechanical properties that are substantially equivalent to those described above for the hydrophobic layer.

The polymers used to form the polymeric films of the present invention may contain other ingredients such as fillers, pigments, and the like as is well known in the art. The only limitation on the use of such other ingredients is that the water contact angles of the polymeric layers fall within the ranges set forth above for the hydrophilic and hydrophobic layers respectively.

For multi-layer structures, the weight of an individual hydrophilic layer is suitably less than about 30% of the weight of the entire film. Preferably, the weight of the hydrophilic layer is suitably less than about 15% of the weight of the entire film. Most preferably, the hydrophilic layer is between about 5% and 10% of the weight of the entire film. If one intermediate layer is used, the weight of the intermediate layer is preferably less than 30% of the weight of the entire film.

It is preferred that the thickness of the entire web is less than 2 mil (0.051 mm). Preferably the thickness is between about 0.5 mil (0.012 mm) and about 2.0 mil (0.051 mm). More preferably, the thickness is between about 0.5 mil (0.012 mm) and about 1.5 mil (0.038 mm). A particularly preferred film has a thickness of about 1 mil (0.025 mm).

Methods of Making

The polymeric film of the present invention may be processed using conventional procedures for producing multilayer films on conventional coextruded film-making equipment. In general, polymers can be melt processed into films using either cast or blown film extrusion methods both of which are described in *Plastics Extrusion Teleology*-2nd Ed., by Allan A. Griff (Van Nostrand Reinhold-1976), which is hereby incorporated herein by reference. Cast film is extruded through a linear slot die. Generally, the flat web is cooled on a large moving polished metal roll (chill roll). It quickly cools, and peels off the first roll, passes over one or more auxiliary rolls, then through a set of rubber-coated pull or "haul-off" rolls, and finally to a winder.

In blown film extrusion the melt is extruded upward through a thin annular die opening. This process is also referred to as tubular film extrusion. Air is introduced through the center of the die to inflate the tube and causes it to expand. A moving bubble is thus formed which is held at constant size by simultaneous control of internal air pressure, extrusion rate, and haul-off speed. The tube of film is cooled by air blown through one or more chill rings surrounding the tube. The tube is next collapsed by drawing it into a flattened frame through a pair of pull rolls and into a winder.

A coextrusion process requires more than one extruder and either a coextrusion feedblock or a multi-manifold die system or combination of the two to achieve the multilayer film structure. U.S. Pat. No. 4,152,387 and 4,197,069, issued May 1, 1979 and Apr. 8, 1980, respectively, both to Cloeren, which are hereby incorporated herein by reference, disclose the feedblock and multi-manifold die principle of coextrusion. Multiple extruders are connected to the feedblock which can employ moveable flow dividers to proportionally change the geometry of each individual flow channel in direct relation to the volume of polymer passing through the flow channels. The flow channels are designed such that, at their point of confluence, the materials flow together at the same velocities and pressure, minimizing interfacial stress and flow instabilities. Once the materials are joined in the feedblock, they flow into a single manifold die as a composite structure. Other examples of feedblock and die systems are disclosed in *Extrusion Dies for Plastics and Rubber*, W. Michaeli, Hanser, New York, $2_{nd}$ Ed., 1992, hereby incorporated herein by reference. It may be important in such processes that the melt viscosities, normal stress differences, and melt temperatures of the material do not differ too greatly. Otherwise, layer encapsulation or flow instabilities may. result in the die leading to poor control of layer thickness distribution and defects from non-planar interfaces (e.g. fish eye) in the multilayer film.

An alternative to feedblock coextrusion is a multi-manifold or vane die as disclosed in aforementioned U.S. Pat. No. 4,152,387 and 4,197,069, as well as U.S. Pat. No. 4,533,308, issued Aug. 6, 1985 to Cloeren, hereby incorporated herein by reference. Whereas in the feedblock system melt streams are brought together outside and prior to entering the die body, in a multi-manifold or vane die each melt stream has its own manifold in the die where the polymers spread independently in their respective manifolds. The melt streams are married near the die exit with each melt stream at full die width. Moveable vanes provide adjustability of the exit of each flow channel in direct proportion to the volume of material flowing through it, allowing the melts to flow together at the same velocity, pressure, and desired width.

Since the melt flow properties and melt temperatures of polymers vary widely, use of a vane die has several advantages. The die lends itself toward thermal isolation characteristics wherein polymers of greatly differing melt temperatures, for example up to 175° F. (80° C.), can be processed together.

Each manifold in a vane die can be designed and tailored to a specific polymer. Thus the flow of each polymer is influenced only by the design of its manifold, and not forces imposed by other polymers. This allows materials with greatly differing melt viscosities to be coextruded into multilayer films. In addition, the vane die also provides the ability to tailor the width of individual manifolds, such that an internal layer can be completely surrounded by the outer layer leaving no exposed edges. The aforementioned patents also disclose the combined use of feedblock systems and vane dies to achieve more complex multilayer structures.

One of skill in the art will recognize that the size of an extruder used to produce the films of the present invention depends on the desired production rate and that several sizes of extruders may be used. Suitable examples include extruders having a 1 (2.5 cm) to 1.5 inch (3.7 cm) diameter with a length/diameter ratio of 24 or 30. If required by greater production demands, the extruder diameter can range upwards. For example, extruders having a diameter between about 2.5 inches (6.4 cm) and about 4 inches (10 cm) can be used to produce the films of the present invention. A general purpose screw may be used. A suitable feedblock is a single temperature zone, fixed plate block. The distribution plate is machined to provide specific layer thicknesses. For example, for a three layer film, the plate provides layers in an 80110/10 thickness arrangement, a suitable die is a single temperature zone flat die with "flex-lip" die gap adjustment. The die gap is typically adjusted to be less than 0.020 inches (0.5 mm) and each segment is adjusted to provide for uniform thickness across the web. Any size die may be used as production needs may require, however, 10–14 inch (25–35 cm) dies have been found to be suitable. The chill roll is typically water-cooled. Edge pinning is generally used and occasionally an air knife may be employed.

For some coextruded films, the placement of a tacky hydrophilic material onto the chill roll may be necessary. When the arrangement places the tacky material onto the chill roll, release paper may be fed between the die and the chill roll to minimize contact of the tacky material with the rolls. However, a preferred arrangement is to extrude the tacky material on the side away from the chill roll. This arrangement generally avoids sticking material onto the chill roll. An extra stripping roll placed above the chill roll may also assist the removal of tacky material and also can provide for additional residence time on the chill roll to assist cooling the film.

Occasionally, tacky material may stick to downstream rolls. This problem may be minimized by either placing a low surface energy (e.g. Teflon®) sleeve on the affected rolls, wrapping Teflon tape on the effected rolls, or by feeding release paper in front of the effected rolls. Finally, if it appears that the tacky material may block to itself on the wound roll, release paper may be added immediately prior to winding. This is a standard method of preventing blocking of film during storage on wound rolls. Processing aids, release agents or contaminants should be minimized. In some cases, these additives can bloom to the surface and reduce the surface energy (raise the contact angle) of the hydrophilic surface.

An alternative method of making the multi-layer films of the present invention is to extrude a web comprising a material suitable for one of the individual layers. Extrusion methods as may be known to the art for forming flat films are suitable. Such webs may then be laminated to form a multi-layer film suitable for formation into a fluid pervious web using the methods discussed below. As will be recognized, a suitable material, such as a hot melt adhesive, can be used to join the webs to form the multi-layer film. A preferred adhesive is a pressure sensitive hot melt adhesive such as a linear styrene isoprene styrene ("SIS") hotmelt adhesive, but it is anticipated that other adhesives, such as polyester of polyamide powdered adhesives, hotmelt adhesives with a compatibilizer such as polyester, polyamide or low residual monomer polyurethanes, other hotmelt adhesives, or other pressure sensitive adhesives could be utilized in making the multi-layer films of the present invention.

In another alternative method of making the multi-layer polymeric films of the present invention, a base or carrier web can be separately extruded and one or more layers can be extruded thereon using an extrusion coating process to form a multi-layer polymeric film according to the present invention. Preferably, the carrier web passes under an extrusion die at a speed that is coordinated with the extruder speed so as to form a very thin film having a thickness of less than about 25 microns. The molten polymer and the carrier web are brought into intimate contact as the molten polymer cools and bonds with the carrier web. As noted above, a tie layer may enhance bonding between the layers. Contact and bonding are also normally enhanced by passing the layers through a nip formed between two rolls. The bonding may be further enhanced by subjecting the surface of the carrier web that is to contact the film to surface treatment, such as corona treatment, as is known in the art and described in *Modern Plastics Encyclopedia Handbook*, p. 236 (1994), which is hereby incorporated by reference.

The Fluid Pervious Web of the Present Invention

Another aspect of the present invention is a fluid pervious web suitable for use as a topsheet in an absorbent article. As is described below, the fluid pervious web of the present invention is preferably formed by macroscopically expanding a polymeric film of the present invention. The fluid pervious web of the present invention contains a plurality of macroapertures, microapertures or both. Macroapertures and/or microapertures give the fluid pervious web a more consumer-preferred fiber-like or cloth-like appearance than webs apertured by methods such as embossing or perforation (e.g. using a roll with a multiplicity of pins) as are known to the art (one of skill in the art will recognize that such methods of providing apertures to a polymeric film are also useful for providing apertures to the films of the present invention). Although the fluid pervious web of the present invention is described herein as a topsheet for use in an absorbent article, one having ordinary skill in the art would recognize that the fluid pervious web of the present invention would have other uses, such as bandages, agricultural coverings, and similar uses where it is desirable to manage fluid flow through a surface.

The macro and microapertures are preferably formed by applying a high pressure fluid jet comprised of water or the like against one surface of the multi-layer polymeric film, preferably while applying a vacuum adjacent the opposite surface of the multi-layer polymeric film. In general, the multi-layer polymeric film is supported on one surface of a forming structure having opposed surfaces. The forming structure is provided with a multiplicity of apertures therethrough which place the opposed surfaces in fluid communication with one another. While the forming structure may be stationary or moving, a preferred embodiment uses the forming structure as part of a continuous process where the multi-layer polymeric film has a direction of travel and the forming structure carries the multi-layer polymeric film in the direction of travel while supporting the film. The fluid jet and, preferably, the vacuum cooperate to provide a fluid pressure differential across the thickness of the film causing the film to be urged into conformity with the forming structure and to rupture in areas that coincide with the apertures in the forming structure.

In particularly preferred embodiments, the multi-layer polymeric film passes over two forming structures in sequence. The first forming structure being provided with a multiplicity of fine scale apertures which, on exposure to the aforementioned fluid pressure differential, cause formation of microapertures in the web of film. The second forming structure exhibits a macroscopic, three-dimensional cross section defined by a multiplicity of macroscopic cross section apertures. On exposure to a second fluid pressure differential the film substantially conforms to the second forming structure while substantially maintaining the integrity of the fine scale apertures.

Such methods of aperturing are known as "hydroformation" and are described in greater detail in commonly assigned U.S. Pat. No. 4,609,518 issued to Curro et al. on Sep. 2, 1986; U.S. Pat. No. 4,629,643 issued to Curro, et al. on Dec. 16, 1986; U.S. Pat. No. 4,637,819 issued to Ouellette, et al. on Jan. 20, 1987; U.S. Pat. No. 4,681,793 issued to Linman, et al. on July 21, 1987; U.S. Pat. No. 4,695,422 issued to Curro, et al. on Sep. 22, 1987; U.S. Pat. No. 4,778,644 issued to Curro, et al. on Oct. 18, 1988; U.S. Pat. No. 4,839,216 issued to Curro, et al. on June 13, 1989; and U.S. Pat. No. 4,846,821 issued to Lyons, et al. on Jul. 11, 1989, the disclosures of each of said patents being incorporated herein by reference.

The apertured web of the present invention may also be formed by methods such as vacuum formation and using mechanical methods such as punching. Vacuum formation is disclosed in U.S. Pat. No. 4,463,045, issued to Ahr, et al. on Jul. 31, 1984, the disclosure of which is hereby incorporated herein by reference. Examples of mechanical methods are disclosed in U.S. Pat. No. 4,798,604, 4,780,352, and 3,566,726 the disclosures of which are incorporated herein by reference.

Figure 4:
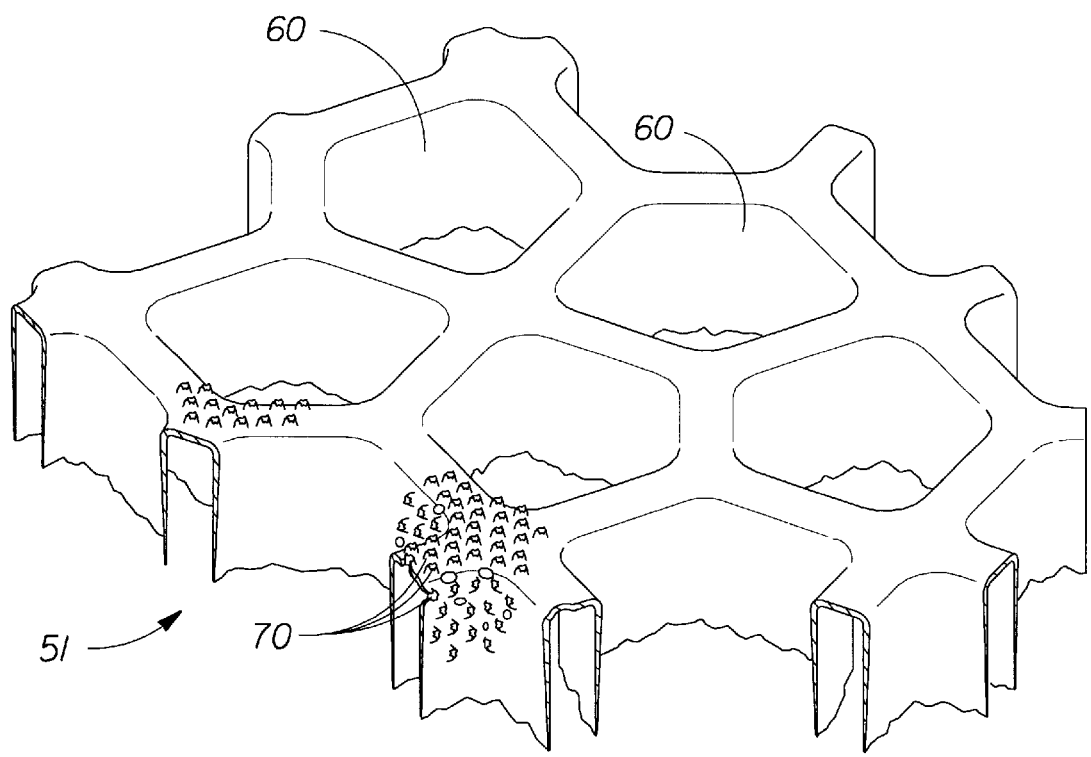
FIG. 4 is a greatly enlarged simplified schematic cross-sectional of a macroscopically expanded, microscopically apertured three-dimensional topsheet according to the present invention.

FIG. 4 is an enlarged partially segmented, perspective illustration of one embodiment of a topsheet 51 according to the present invention, the topsheet comprising both macroapertures 60 and microapertures 70. For the sake of clarity, microapertures 70 are not illustrated across the entire surface of the topsheet although the microapertures would typically extend across the entire topsheet.

Figure 5:
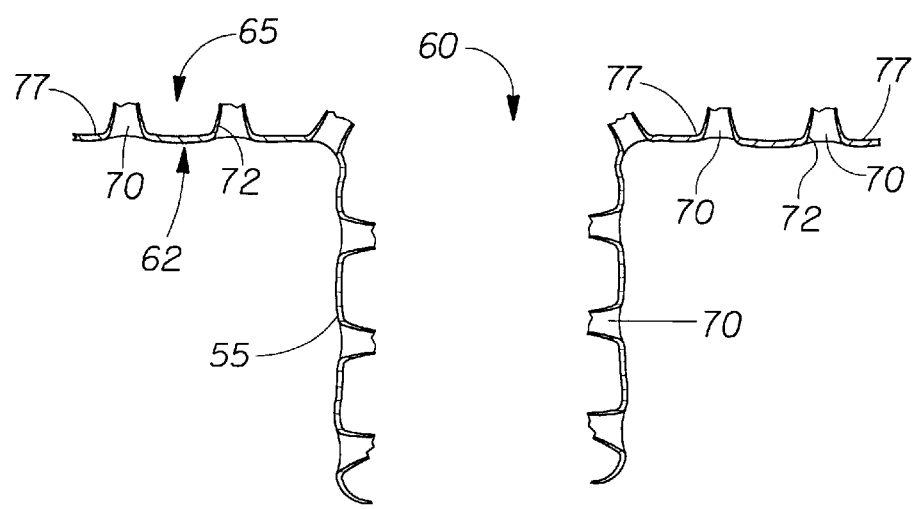
FIG. 5 is an enlarged cross-sectional view showing one arrangement of microapertures and macroapertures according to the present invention.

If both microapertures and macroapertures are employed, several different arrangements of macro and microapertures may be used. A preferred arrangement of apertures is depicted in FIG. 5, and is referred to as a female structure because the sides 55 of the macroapertures 60 extend away from the wearer-contacting surface 65 of the topsheet. The combination of macro and microapertures is formed using a two-step hydroformation process. In the first step, microapertures 70, are formed in the polymeric film by subjecting the polymeric film to a high pressure water stream while the polymeric film is supported by a metal screen having apertures corresponding in size to the desired size of the apertures to be formed in the polymeric film. In the second step, the polymeric film containing the microapertures is again subjected to hydroformation to form the macroapertures. The macroapertures may be formed by perforating the polymeric film in the same or opposite direction as the microapertures were formed. In the female structure shown in FIG. 5, the macroapertures have been formed in the direction opposite from the microapertures.

Figure 6:
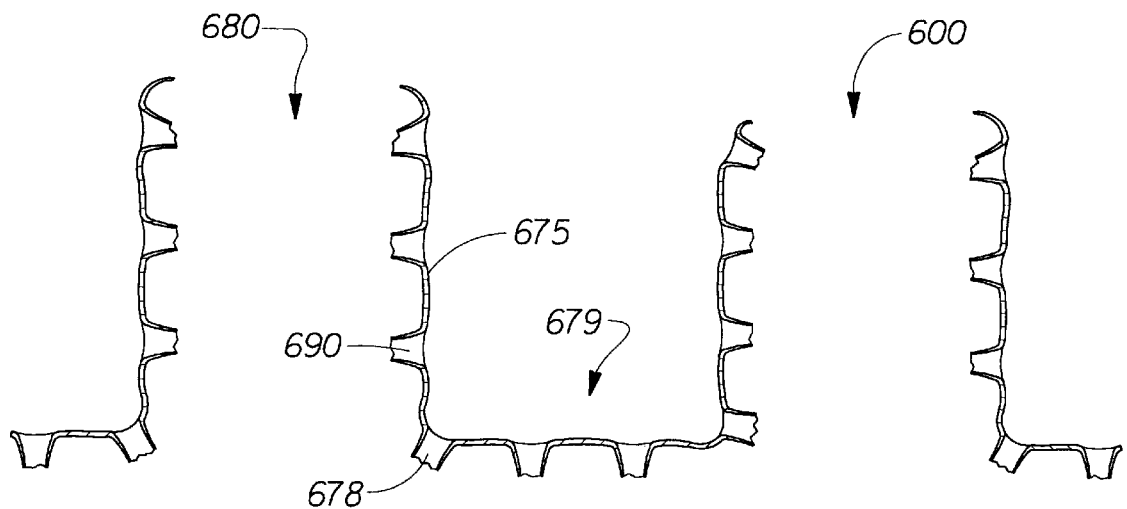
FIG. 6 is an enlarged cross-sectional view showing another arrangement of microapertures and macroapertures according to the present invention.
Figure 7:
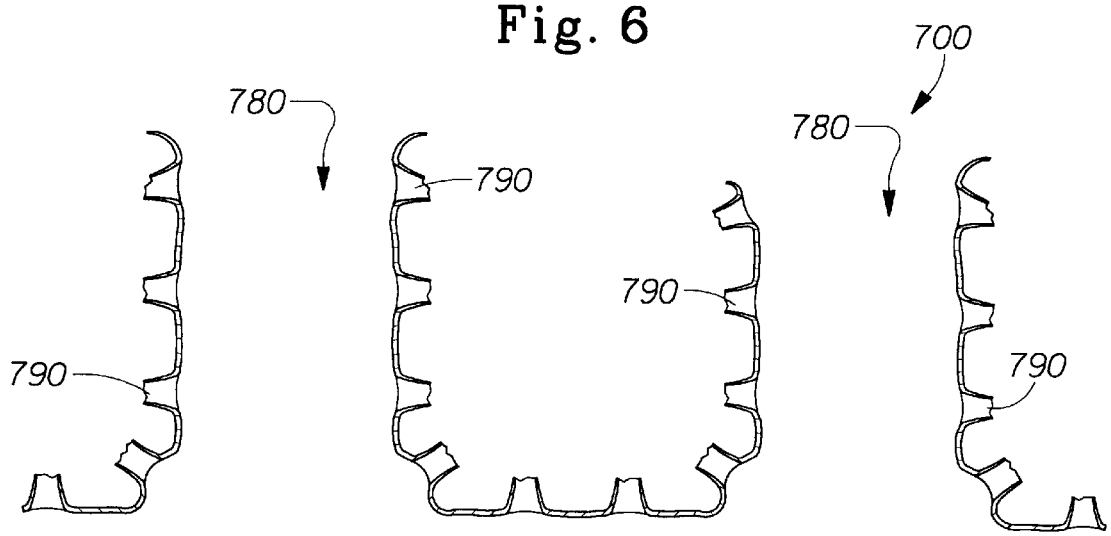
FIG. 7 is an enlarged cross-sectional view showing another arrangement of microapertures and macroapertures according to the present invention.

FIG. 6 depicts another structure suitable for use in the topsheet of the present invention. This structure is referred to as a male structure. As with the female structure, the male structure comprises a combination of macroapertures 680 and microapertures 690 formed by hydroformation. The male structure differs from the female structure in that the sides 675 of the macroapertures 680 extend outwardly away from the wearer-contacting or first surface 679 and toward the wearer. FIG. 6 depicts a male web structure 600 in which the macroapertures 680 were formed in the opposite direction as the microapertures 690. FIG. 7 is a male web structure 700 in which the macroapertures 780 were formed in same direction as the microapertures 790. If only macroapertures or microapertures are formed in the topsheet of the present invention, they may either be in the male or female orientation. It is important however that the apertures are formed so that the hydrophilic layer is on the inside surface of the apertures to ensure fluid acquisition.

Figure 8:
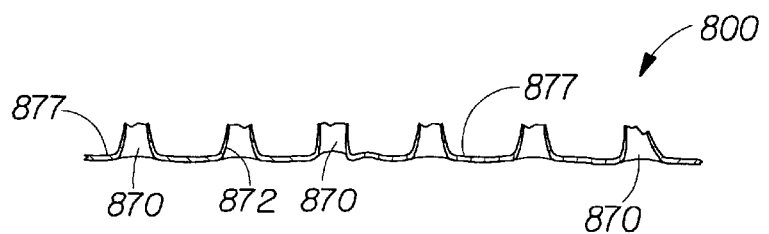
FIG. 8 is an enlarged cross-sectional view showing an arrangement of microapertures according to the present invention.
Figure 9:
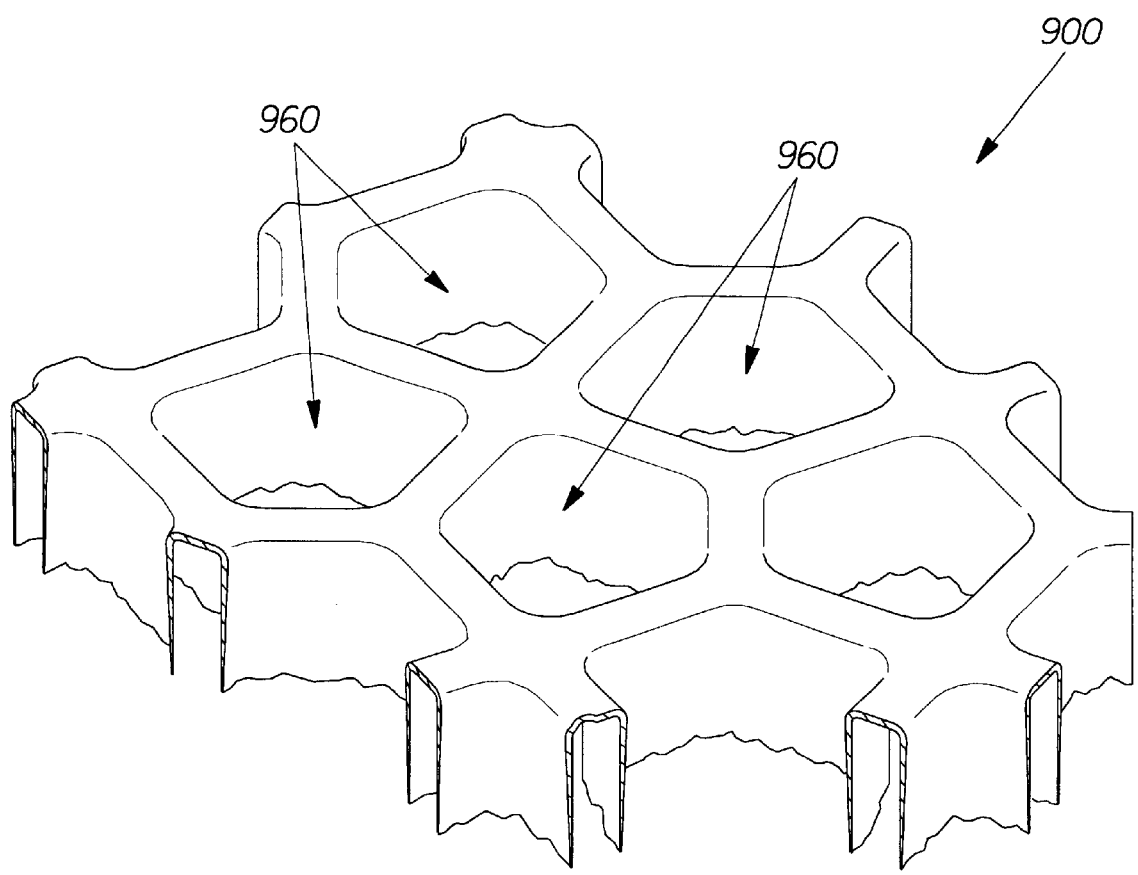
FIG. 9 is a greatly enlarged simplified schematic cross-sectional of a macroscopically expanded, three-dimensional topsheet according to the present invention.

The polymeric film of the present invention can also be provided with either microapertures or macroapertures. FIG. 8 depicts a cross-sectional view of a web structure 800 according to the present invention in which only microapertures 870 have been formed. FIG. 9 depicts a web structure 900 according to the present invention in which only macroapertures 960 have been formed (One of skill in the art will recognize that such macroapertures can be formed using other methods (e.g. vacuum forming) in addition to hydroforming as discussed above.

The size of the macroapertures may be varied. Preferably, the macroapertures have a cone like shape with the base of the cone, which is proximal to the outer surface of the layer, having a diameter of about 2 millimeters and the top of the cone, which is distal to the outer surface of the layer, having a diameter of about 1 millimeter. In addition, it is preferred that the topsheet have 24 macroapertures per square centimeter. The size of the microapertures may also be varied, however, it is preferred that the microapertures are formed using a 100 mesh screen.

The performance properties of the topsheet of the present invention may be manipulated depending on the orientation of the hydrophilic block copolymer layer and the hydrophobic layer in the polymeric film from which the topsheet is formed. As described above, the polymeric film of the present invention may comprise any number of layers. The topsheet may be formed so that the wearer-contacting surface is a hydrophobic layer and the garment-facing surface is hydrophilic (known as "phobic/philic"), or so that the wearer-contacting surface is hydrophilic and the garment facing surface is hydrophobic (known as "philic/phobic"). In addition, by varying both the orientation of the hydrophilic and hydrophobic layers as well as the aperture structure (i.e., female or male), many different topsheet structures, with different advantageous properties, can be formed according to the present invention.

The preferred topsheet orientation, shown in FIG. 5, is one in which the wearer-contacting surface or first surface 65 is hydrophobic, the opposed garment-facing surface or second surface 62 is hydrophilic, and the aperture structure is female. When the polymeric film of the present invention is apertured to form a topsheet with female structure (as shown in FIG. 5), the inside surfaces 72 of the microapertures are predominately hydrophilic layers and the land areas 77 between the microapertures on the wearer-contacting surface 65 are hydrophobic. As described below, this arrangement creates a surface energy gradient between the lands 77 and the interior of the microapertures. This gradient helps move a droplet of liquid from the lands into the microapertures 70 and thus away from the wearer-contacting surface 65 and toward the absorbent core of the absorbent article. Of course, other combinations of layers and aperture configurations are possible and such combinations are part of the present invention.

Figure 10:
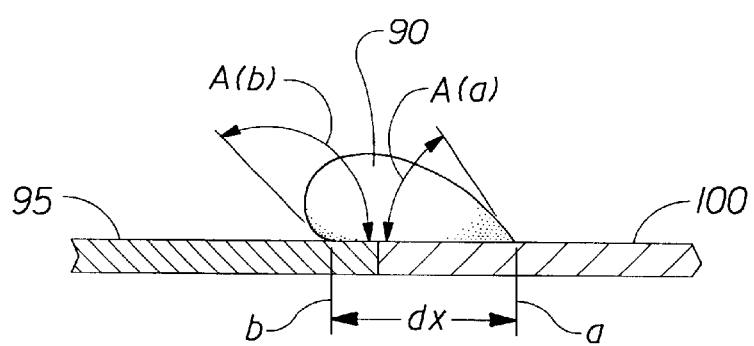
FIG. 10 is an enlarged cross-sectional view of a droplet of liquid on a solid surface having two different surface energies, thus exhibiting two different water contact angles A(a) and A(b).

Whenever the wearer-contacting surface and the garment-facing surface of the topsheet of the present invention comprise materials having different surface properties (eg., one of the layers is hydrophobic and the other is hydrophilic), a surface energy gradient is created. Surface energy gradients have been found to be useful in promoting fluid transport. FIG. 10 illustrates a droplet of fluid 90 which is located on a solid surface having two regions 95 and 100 having differing surface energies (indicated by the different cross-hatching for illustrative purposes). In the situation illustrated in FIG. 6, region 95 exhibits a comparatively lower surface energy than region 100, and hence a reduced wettability for the fluid of the droplet than region 100. Accordingly, the droplet 90 produces a water contact angle A(b) at the edge of the droplet contacting region 95 which is greater than the water contact angle A(a) produced at the edge of the droplet contacting region 100. It should be noted that although for graphic clarity the points "a" and "b" lie in a plane, the distance "dx" between points "a" and "b" need not be linear, instead representing the extent of droplet/surface contact regardless of the shape of the surface. Droplet 90 thus experiences a surface energy imbalance and hence an external force due to the differences in the relative surface energies (i.e., a surface energy gradient) between regions 95 and 100, which can be represented by the equation (3):

$$dF = G[\cos A(a) - \cos A(b)]dx \qquad (3)$$

where:

dF is the net force on the fluid droplet, dx is the distance between the reference locations "a" and "b", G is as defined previously, and A(a), and A(b) are the water contact angles A at locations "a" and "b", respectively. Solving equation (1) for cos A(a) and cos A(b) and substituting into equation (3) yields equation (4):

$$dF = G[(W(a)/G - 1) - (W(b)/G - 1)]dx \qquad (4)$$

Equation (4) can be simplified to equation (5):

$$dF = (W(a) - W(b))dx \qquad (5)$$

The importance of the differential in surface energy between the two surfaces is clearly depicted in equation (5), as is the directly proportional effect that changes in the magnitude of the differential in work of adhesion would have on the magnitude of the force.

More detailed discussions of the physical nature of surface energy effects and capillarity may be found in *Textile Science and Technology*, Volume 7, *Absorbency*, edited by Portnoy K. Chatteijee (1985), and *Capillarity. Theory and Practice, Ind. Eng. Chem.* 61,10 (1969) by A. M. Schwartz, which are hereby incorporated herein by reference.

Accordingly, the force experienced by a droplet will tend to cause movement in the direction of the higher surface energy region. For simplicity and graphic clarity, the surface energy gradient is provided by a single, sharp discontinuity or boundary between well-defined regions of constant but differing surface energy as shown in FIG. 10. Surface energy gradients may also exist as a continuous gradient or a step-wise gradient, with the force exerted on any particular droplet (or portions of such droplet) being determined by the surface energy at each particular area of droplet contact.

By having a polymeric film with a surface energy gradient formed by structures creating a relatively low surface energy adjacent the portion of the topsheet film which will be placed adjacent to and in contact with the wearer's skin, and a relatively higher surface energy portion located away from contact with the wearer's skin, the topsheet will be capable of moving a drop of liquid from the portion of the topsheet exhibiting the relatively lower surface energy to the portion of the topsheet exhibiting the relatively higher surface energy. The motion of the drop of liquid is induced by the surface forces which also cause a water contact angle differential between the lower surface energy portion and the higher surface energy portion. It is believed that this resulting surface energy gradient, which enhances the fluid handling properties of the topsheet of the present invention, makes the topsheet well suited for use as a topsheet on an absorbent article.

In addition to the enhanced fluid handling properties, by designing topsheet so that its relatively lower surface energy portion can be placed in contact with the wearer's skin, the adhesion between the skin and the topsheet is reduced by decreasing the capillary force generated by occlusive body fluids located between the first surface of the topsheet and the wearer's skin. By providing a structure with reduced adhesion between the wearer's skin and the topsheet, the sensation or impression of stickiness associated with adhesion to a plastic topsheet is also reduced.

The potential for rewet is also reduced by having a topsheet with a surface energy gradient according to the aforementioned description. As use forces tend to force the collected fluid to rewet or be squeezed out of the pad (e.g., squeezed by compression from the absorbent core towards the first surface of the topsheet), such undesirable movement will be resisted by the first surface of the topsheet which has a relatively low surface energy to repel the fluid as it attempts to make its way out of the pad through the openings in the topsheet. That is, a surface energy gradient provides a thermodynamic barrier against fluid flow that can cause rewet.

With regard to the surface energy gradient according to the present invention, it is important to remember that the upper and lower bounds of any such gradient are relative with respect to one another, i.e., the regions of a multi-layer polymeric film whose interface defines a surface energy gradient need not be on different sides of the hydrophobic/hydrophilic spectrum. That is to say, a gradient may be established by two surfaces of diverse degrees of hydrophobicity or diverse degrees of hydrophilicity, and need not necessarily be established with regard to a hydrophobic surface and a hydrophilic surface. Notwithstanding the foregoing, it is presently preferred that the upper surface of the multi-layer polymeric film have a comparatively low surface energy, i.e., that it be generally hydrophobic, in order to maximize the driving force imparted to the incoming fluid and minimize the overall wettability of the wearer-contacting layer.

While a surface energy gradient as described above may be provided by the multi-layer films of the present invention, such gradients can also be provided or enhanced by microscopic spaced apart depositions of a low surface energy material. Such depositions are discussed in detail in the aforementioned U. S. Pat. No. 6,025,049, issued Feb. 15, 2000. For example, if such depositions are applied to the land areas discussed above, the surface energy gradient between the depositions and the hydrophilic portions of the web can be greater than the gradient between the lands and the portions with an increase in the force tending to direct fluids toward the apertures. Similarly, treating a web where both surfaces are hydrophilic (monolayer or multilayer film) would provide such webs with a surface energy gradient. A suitable coating material is a silicone resin that imparts a relatively lower surface energy to the surface on which it is applied. A suitable silicone resin is from Dow Corning of Midland, Mich. available as Syl-Off 7677 to which a crosslinker, available as Syl-Off 7048, is added in proportions by weight of 100 parts to 10 parts, respectively. Another suitable surface treatment is a coating of a UV curable silicone comprising a blend of two silicones commercially available from General Electric Company, Silicone Products Division, of Waterford, N.Y., under the designations UV 9300 and UV 9380C-D1, in proportions by weight of 100 parts to 2.5 parts, respectively.

For example, referring to FIG. 8, a multiplicity of low surface energy depositions (not shown) could be disposed on land areas 877 and portions of the microaperture walls 872 of the web 800 shown therein. As discussed above, such depositions can enhance the surface energy gradient between hydrophilic portions of the web and hydrophobic portions of the web 800.

Absorbent Article According to the Present Invention

As used herein, the term "absorbent article" refers to devices which absorb and contain body exudates, and, more specifically, refers to devices which are placed against or in proximity to the body of the wearer to absorb and contain the various exudates discharged from the body. The term "disposable" is used herein to describe absorbent articles which are not intended to be laundered or otherwise restored or reused as an absorbent article (i.e., they are intended to be discarded after a single use, and, preferably, to be recycled, composted or otherwise disposed of in an environmentally compatible manner). A "unitary" absorbent article refers to absorbent articles which are formed of separate parts united together to form a coordinated entity so that they do not require separate manipulative parts like a separate holder and pad.

Figure 11:
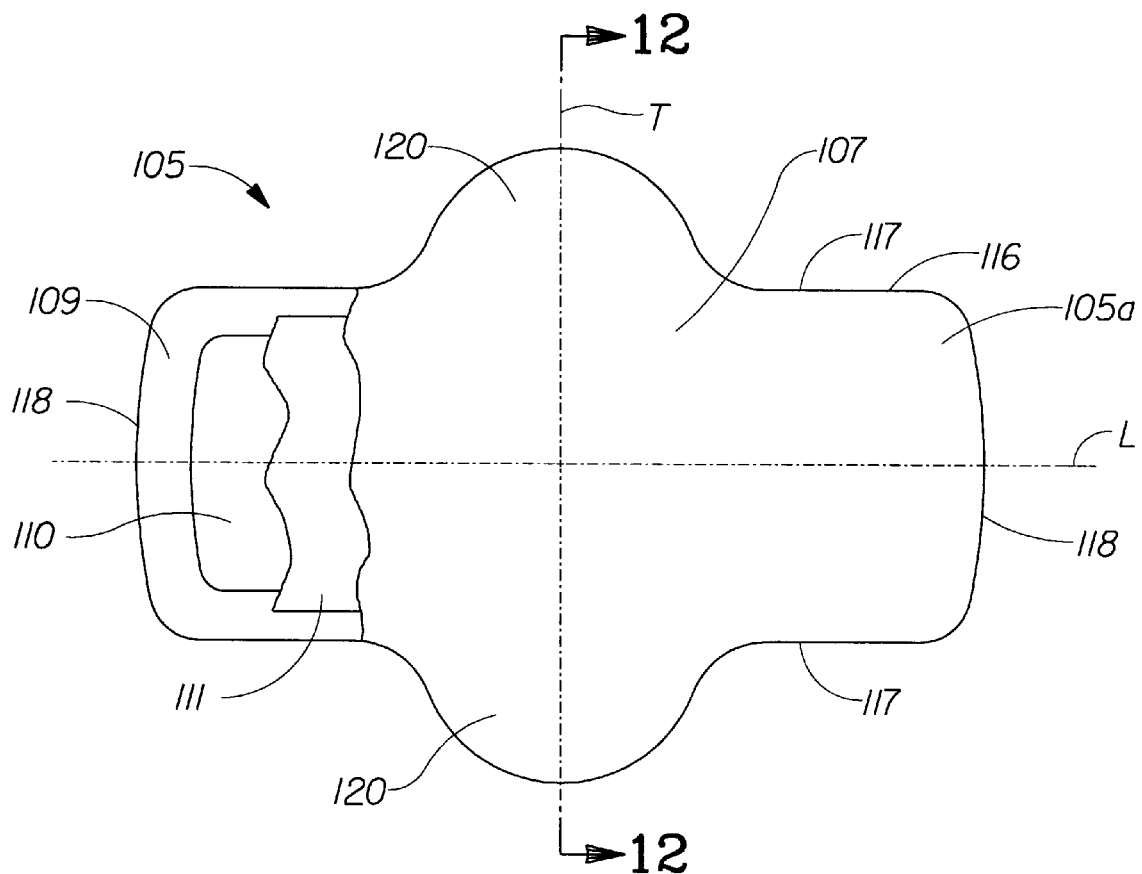
FIG. 11 a top plan view of a sanitary napkin with portions of the sanitary napkin cut away to more clearly show the construction of the sanitary napkin.

A preferred embodiment of a unitary disposable absorbent article made in accordance herewith is the catamenial pad, sanitary napkin 105, shown in FIG. 11. As used herein, the term "sanitary napkin" refers to an absorbent article which is worn by females adjacent to the pudendal region, generally external to the urogenital region, and which is intended to absorb and contain menstrual fluids and other vaginal discharges from the wearer's body (e.g., blood, menses, and urine). Interlabial devices which reside partially within and partially external to the wearer's vestibule are also within the scope of this invention.

It is to be understood that the overall size, shape, and/or configuration of the absorbent article, if any, into which fluid transport multi-layer polymeric films according to the present invention are incorporated, or utilized in conjunction with, have no criticality or functional relationship to the principles of the present invention. Such parameters, however, must be considered along with the intended fluid and intended functionality when determining appropriate multi-layer polymeric film configurations and appropriate orientation of surface energy gradients according to the present invention.

Sanitary napkin 105 is illustrated as having two surfaces such as first surface 105a, sometimes referred to as a wearer-contacting or facing surface, a body-contacting or facing surface or "body surface", and second surface 105b, sometimes referred to as a garment-facing or contacting surface, or "garment surface". The sanitary napkin 105 is shown in FIG. 11 as viewed from its first surface 105a. The first surface 105a is intended to be worn adjacent to the body of the wearer. The second surface 105b of the sanitary napkin 105 (shown in FIG. 12) is on the opposite side and is intended to be placed adjacent to the wearer's undergarment when the sanitary napkin 105 is worn.

The sanitary napkin 105 has two centerlines, a longitudinal centerline "L" and a transverse centerline "T". The term "longitudinal", as used herein, refers to a line, axis or direction in the plane of the sanitary napkin 105 that is generally aligned with (e.g., approximately parallel to) a vertical plane which bisects a standing wearer into left and right body halves when the sanitary napkin 105 is worn. The terms "transverse" or "lateral" as used herein, are interchangeable and refer to a line, axis or direction which lies within the plane of the sanitary napkin 105 that it generally perpendicular to the longitudinal direction. FIG. 11 also shows that the sanitary napkin 105 has a periphery 116 which is defined by the outer edges of the sanitary napkin 105 in which the longitudinal edges (or "side edges") are designated 117 and the end edges (or "ends") are designated 118.

FIG. 11 is top plan view of a sanitary napkin 105 of the present invention in a substantially flat state with portions of the sanitary napkin being cut away to more clearly show the construction of the sanitary napkin 105 and with the portion of the sanitary napkin 105 which faces or contacts the wearer 105a oriented towards the viewer. As shown in FIG. 11, the sanitary napkin 105 preferably comprises a liquid pervious topsheet 107, a liquid impervious backsheet 109 joined with the topsheet 107, an absorbent core 110 positioned between the topsheet 107 and the backsheet 109, and a secondary topsheet or acquisition layer 111 positioned between the topsheet 107 and the absorbent core 110.

The sanitary napkin 105 preferably includes optional side flaps or "wings" 120 that are folded around the crotch portion of a wearer's panty. The side flaps 120 can serve a number of purposes, including, but not limited to helping to hold the napkin in proper position while protecting the wearer's panty from soiling and keeping the sanitary napkin secured to the wearer's panty.

Figure 12:
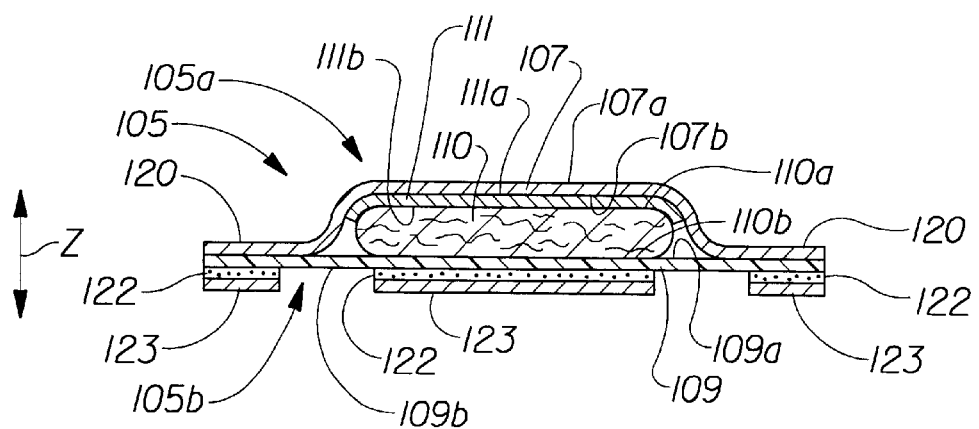
FIG. 12 is a cross-sectional view of the sanitary napkin of FIG. 11 taken along section line 12—12.

FIG. 12 is a cross-sectional view of the sanitary napkin 105 taken along section line 12—12 of FIG. 11. As can be seen in FIG. 12, the sanitary napkin 105 preferably includes an adhesive fastening means 122 for attaching the sanitary napkin 105 to the undergarment of the wearer. Removable release liners 123 cover the adhesive fastening means 122 to keep the adhesive from sticking to a surface other than the crotch portion of the undergarment prior to use.

The topsheet 107 comprises the apertured formed film web of the present invention as is described above so as to provide the comfort and fluid handling benefits of the present invention.

The topsheet 107 has a first surface 107a and a second surface 107b positioned adjacent to and preferably secured to a first surface 111a of the fluid acquisition layer 111 to promote fluid transport from the topsheet to the acquisition layer. The second surface 111b of the acquisition layer 111 is positioned adjacent to and is preferably secured to the first surface 110a of an absorbent core or fluid storage layer 110 to promote fluid transport from the acquisition layer to the absorbent core. The second surface 110b of the absorbent core 110 is positioned adjacent to and is preferably secured to the first surface 109a of the backsheet 109.

In addition to having a longitudinal direction and a transverse direction, the sanitary napkin 105 also has a "Z" direction or axis, which is the direction proceeding downwardly through the topsheet 107 and into whatever fluid storage layer or core 110 that may be provided. The objective is to provide a substantially continuous path between the topsheet 107 and the underlying layer or layers of the absorbent article herein, such that fluid is drawn in the "Z" direction and away from the topsheet of the article and toward its ultimate storage layer.

The absorbent core 110 may be any absorbent means which is capable of absorbing or retaining liquids (e.g., menses and/or urine). As shown in FIGS. 7 and 8, the absorbent core 110 has a body surface 110a, a garment facing surface 110b side edges, and end edges. The absorbent core 110 may be manufactured in a wide variety of sizes and shapes (e.g. rectangular, oval, hourglass, dogbone, asymmetric, etc.) and from a wide variety of liquid absorbent materials commonly used in sanitary napkins and other absorbent articles such as comminuted wood pulp which is generally referred to as airfelt. Examples of other suitable absorbent materials include creped cellulose wadding; meltblown polymers including coform; chemically stiffened, modified or cross-linked cellulosic fibers; synthetic fibers such as crimped polyester fibers; peat moss; tissue including tissue wraps and tissue laminates; absorbent foams; absorbent sponges; superabsorbent polymers; absorbent gelling materials; or any equivalent material or combination of materials, or mixtures of these.

The configuration and construction of the absorbent core may also be varied (e.g., the absorbent core may have varying caliper zones (e.g. profiled so as to be thicker in the center), hydrophilic gradients, superabsorbent gradients or lower density or lower average basis weight acquisition zones; or may comprise one or more layers or structures). The total absorbent capacity of the absorbent core, should, however, be compatible with the design loading and the intended use of the absorbent article. Further, the size and absorbent capacity of the absorbent core may be varied to accommodate different uses such as incontinent pads, pantiliners, regular sanitary napkins, or overnight sanitary napkins.

Exemplary absorbent structures for use as the absorbent core in the present invention are described in U.S. Pat. No. 4,950,264 issued to Osborn on Aug. 21, 1990; U.S. Pat. No. 4,610,678 issued to Weisman et al. on Sep. 9, 1986; U.S. Pat. No. 4,834,735 issued to Alemany et al. on May 30, 1989; European Patent Application No. 0 198 683, the Procter & Gamble Company, published Oct. 22, 1986 in the name Duenk, et al.; and U.S. patent application Ser. No. 60/128, 352, filed in the name of Noel, et al. Apr. 8, 1999. The disclosure of each of these patents is incorporated herein by reference.

The backsheet 109 and the topsheet 107 are positioned adjacent the garment facing surface and the body facing surface respectively of the absorbent core 110 and are preferably joined thereto and to each other by attachment means (not shown) such as those well known in the art. For example, the backsheet 109 and/or the topsheet 107 may be secured to the absorbent core or to each other by a uniform continuous layer of adhesive, a patterned layer of adhesive or any array of separate lines, spirals or spots of adhesive. Adhesives which have been found to be satisfactory are manufactured by H.B. Fuller Company of St. Paul, Minn. under the designation HL-1258, and by Findlay of Minneapolis, Minn., under the designation H-2031. The attachment means will preferably comprise an open pattern network of filaments of adhesive as disclosed in U.S. Pat. No. 4,573,986 issued to Minetola et al. on Mar. 4, 1986, the disclosure of which is incorporated herein by reference. An exemplary attachment means of an open patterned network of filaments comprises several lines of adhesive filaments swirled into a spiral pattern such as illustrated by the apparatus and method shown in U.S. Pat. No. 3,911,173 issued to Sprague, Jr. on Oct. 7, 1975; U.S. Pat. No. 4,785,996 issued to Zieker, et al. on Nov. 22, 1978 and U.S. Pat. No. 4,842,666 issued to Werenicz on Jun. 27, 1989. The disclosures of each of these patents are incorporated herein by reference. Alternatively, the attachment means may comprise heat bonds, pressure bonds, ultrasonic bonds, dynamic mechanical bonds or any other suitable attachment means or combinations of these attachment means as are known in the art.

Preferably, the topsheet 107 is sized to coincide with the backsheet 109 and joined thereto about the periphery 116 of sanitary napkin 105. The topsheet 107 and the backsheet 109 may be joined using means as are known to the art such as adhesive bonding, heat bonds, pressure bonds, ultrasonic bonds, dynamic mechanical bonds or any other suitable attachment means or combinations of these attachment means as are known in the art. Preferably, the topsheet 107 and the backsheet 109 are joined using a combination of heat and pressure known as fusion bonding.

The backsheet 109 is impervious to liquids (e.g., menses and/or urine) and is preferably manufactured from a thin plastic film, although other flexible liquid impervious materials may also be used. As used herein, the term "flexible" refers to materials which are compliant and are more readily conformed to the general shape and contours of the human body. The backsheet 109 prevents the exudates absorbed and contained in the absorbent core from wetting articles which contact the sanitary napkin 105 such as undergarments and other articles of clothing. The backsheet 109 may thus comprise a woven or nonwoven material, polymeric films such as thermoplastic films of polyethylene or polypropylene, or composite materials such as a film-coated nonwoven material. Preferably, the backsheet of the polyethylene film having a thickness of from about 0.012 mm (0.5 mil) to about 0.051 mm (2.0 mil). Exemplary polyethylene films are manufactured by Clopay Corporation of Cincinnati, Ohio, under the designation P18-1401 and by Tredegar Film Products of Terre Haute, Ind., under the designation XP-9818. The backsheet is preferably embossed and/or matte finished to provide a more cloth-like appearance. Further, the backsheet 109 may permit vapors to escape from the absorbent core 110 (i.e., breathable) while still preventing exudates from passing through the backsheet 109.

In use, the sanitary napkin 105 can be held in place by any support means or attachment means 122 well-known for such purposes. Preferably, the sanitary napkin is placed in the user's undergarment or panty and secured thereto by a fastener such as an adhesive. The adhesive provides a means for securing the sanitary napkin in the crotch portion of the panty. Thus, a portion or all of the outer or garment facing surface 109b of the backsheet 109 is coated with adhesive. Any adhesive or glue used in the art for such purposes can be used for the adhesive herein, with pressure-sensitive adhesives being preferred. Suitable adhesives are manufactured by H. B. Fuller Company of St. Paul, Minn., under the designation 2238. Suitable adhesive fasteners are also described in U.S. Pat. No. 4,917,697. Before the sanitary napkin is placed in use, the pressure-sensitive adhesive is typically covered with a removable release liner 123 in order to keep the adhesive from drying out or adhering to a surface other than the crotch portion of the panty prior to use. Suitable release liners are also described in the above-referenced U.S. Pat. No. 4,917,697. Any commercially available release liners commonly used for such purposes can be utilized herein. A non-limiting example of a suitable release liner is BL30MG-A Silox 4P/O, which is manufactured by the Akrosil Corporation of Menasha, WI. The sanitary napkin 105 of the present invention is used by removing the release liner and thereafter placing the sanitary napkin in a panty so that the adhesive contacts the panty. The adhesive maintains the sanitary napkin in its position within the panty during use.

In one preferred embodiment of the present invention, the sanitary napkin has two flaps 120 each of which are adjacent to and extend laterally from the side edge of the absorbent core. The flaps 120 are configured to drape over the edges of the wearer's panties in the crotch region so that the flaps are disposed between the edges of the wearer's panties and the thighs. The flaps serve at least two purposes. First, the flaps help serve to prevent soiling of the wearer's body and panties by menstrual fluid, preferably by forming a double wall barrier along the edges of the panty. Second, the flaps are preferably provided with attachment means on their garment surface so that the flaps can be folded back under the panty and attached to the garment facing side of the panty. In this way, the flaps serve to keep the sanitary napkin properly positioned in the panty. The flaps can be constructed of various materials including materials similar to the topsheet, backsheet, tissue, or combination of these materials. Further, the flaps may be a separate element attached to the main body of the napkin or can comprise extensions of the topsheet and backsheet (i.e., unitary). A number of sanitary napkins having flaps suitable or adaptable for use with the sanitary napkins of the present invention are disclosed in U.S. Pat. No. 4,687,478, issued to Van Tilburg on Aug. 18, 1987; and U.S. Pat. No. 4,589,876, issued to Van Tilburg on May 20, 1986. The disclosure of each of these patents is hereby incorporated herein by reference.

In a prefferred embodiment of the present invention shown in FIGS. 11 and 12, an acquisition layer(s) 111 is positioned between the topsheet 107 and the absorbent core 110. The acquisition layer 111 may serve several functions including improving wicking of exudates over and into the absorbent core. There are several reasons why the improved wicking of exudates is important, including providing a more even distribution of the exudates throughout the absorbent core and allowing the sanitary napkin 105 to be made relatively thin. The wicking referred to herein may emcompass the transportation of liquids in one, two or all directions (i.e., in the x-y plane and/or in the z-direction). The acquisition layer may be comprised of several different materials including nonwoven or woven polymeric films of synthetic fibers including polyester, poly propylene, or polyethylene; natural fibers including cotton or cellulose; blends of such fibers; or any equivalent materials or combinations of materials. Exaamples of sanitary napkins having an acquisition layer and a topsheet are more fully described in U.S. Pat. No. 4,959,264 issue to Osborn and U.S. Pat. application ser. No. 07/810,774, filed Dec. 17, 1991, now abandoned, in the names of Cree, et al. The disclosures of each of these references are hereby incorporated herein by reference. In a preferred embodiment, the acquisition layer may be joined with the topsheet by any of the conventional means for joining polymeric films together, most preferably by fusion bonds as is more fully described in the above-reference Cree application.

Figure 13:
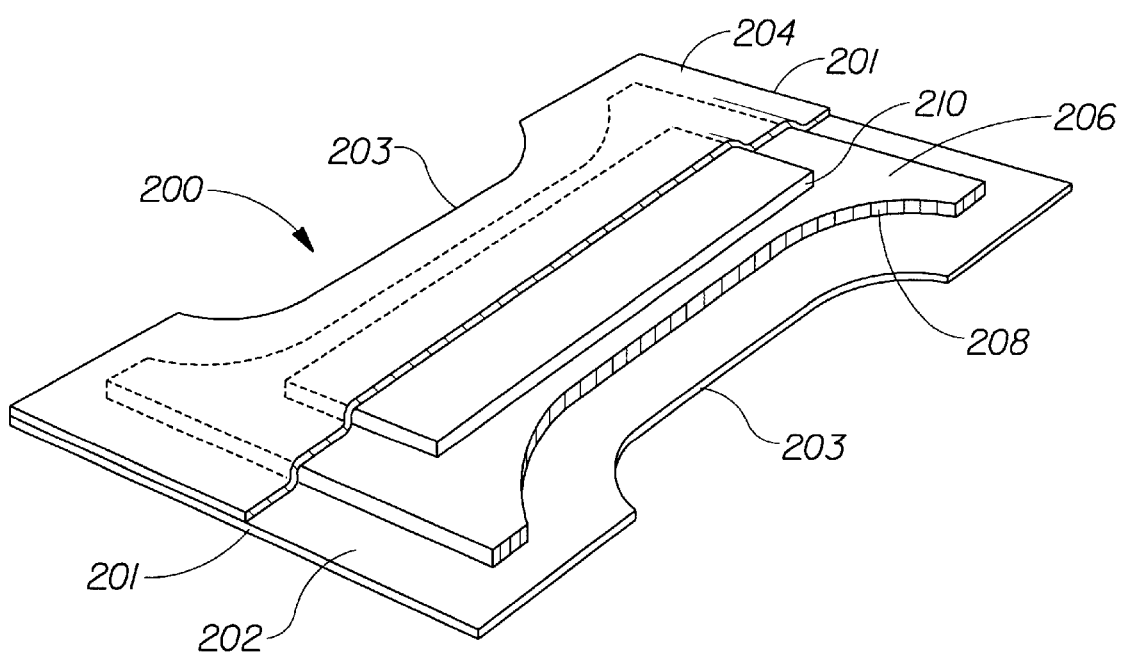
FIG. 13 is an enlarged, partially segmented, perspective illustration of a representative absorbent article in the form of a diaper made in accordance with the present invention.

A representative embodiment of a disposable absorbent article in the form of a diaper 200, is shown in FIG. 13. As used herein, the term "diaper" refers to a garment generally worn by infants and incontinent persons that is worn about the lower torso of the wearer. It should be understood, however, that the present invention is also applicable to other absorbent articles such as incontinent briefs, training pants, diaper inserts, and the like. The diaper 200 depicted in FIG. 13 is a simplified absorbent article that could represent a diaper prior to its being placed on a wearer. It should be understood, however, that the present invention is not limited to the particular type or configuration of diaper shown in FIG. 13.

FIG. 13 is a perspective view of the diaper 200 in its uncontracted state (i.e., with all the elastic induced contraction removed) with portions of the structure being cut-away to more clearly show the construction of the diaper 200. The portion of the diaper 200 which contacts the wearer faces the viewer. The diaper 200 is shown in FIG. 13 to preferably comprise a liquid pervious topsheet 204; a liquid impervious backsheet 202 joined with the topsheet 204; and an absorbent core 206 positioned between the topsheet 204 and the backsheet 202. Additional structural features such as elastic members and fastening means for securing the diaper in place upon a wearer (such as tape tab fasteners) may also be included.

While the topsheet 204, the backsheet 202, and the absorbent core 206 can be assembled in a variety of well known configurations, a preferred diaper configuration is described generally in U.S. Pat. No. 3,860,003 (Buell), issued Jan. 14, 1975, the disclosure of which is incorporated by reference. Alternatively preferred configurations for disposable diapers herein are also disclosed in U.S. Pat. No. 4,808,178 (Aziz et al), issued Feb. 28, 1989; U.S. Pat. 4,695,278 (Lawson), issued Sep. 22, 1987; and U.S. Pat. No. 4,816,025 (Foreman), issued Mar. 28, 1989, the disclosures of each of these patents hereby being incorporated herein by reference.

FIG. 13 shows a preferred embodiment of the diaper 200 in which the topsheet 204 and the backsheet 202 are co-extensive and have length and width dimensions generally larger than those of the absorbent core 206. The topsheet 204 is joined with and superimposed on the backsheet 202 thereby forming the periphery of the diaper 200. The periphery defines the outer perimeter or the edges of the diaper 200. The periphery comprises the end edges 201 and the longitudinal edges 203.

The backsheet 202 is generally that portion of the diaper 200 which prevents the exudates absorbed and contained therein from soiling articles which may contact the diaper 200, such as bedsheets and undergarments. In preferred embodiments, the backsheet 202 is impervious to liquids (e.g., urine) and comprises a thin plastic film such as a thermoplastic film having a thickness of about 0.012 mm (0.5 mil) to about 0.051 mm (2.0 mils). Suitable backsheet films include those manufactured by Tredegar Industries Inc. of Terre Haute, Ind. and sold under the trade names X15306, X10962 and X10964. Other suitable backsheet materials may include breathable materials which permit vapors to escape from the diaper 200 while still preventing exudates from passing through the backsheet 202. Exemplary breathable materials may include materials such as woven webs, nonwoven webs, composite materials such as film-coated nonwoven webs, microporous films such as manufactured by Mitsui Toatsu Co., of Japan under the designation ESPOIR NO and by Exxon Chemical Co., of Bay City, Tex., under the designation EXXAIRE, and monolithic films such as manufactured by Clopay Corporation, Cincinnati, Ohio under the name HYTREL blend P18-3097. Some breathable composite materials are described in greater detail in PCT Application No. WO 95/16746, published on Jun. 22, 1995 in the name of E. I. DuPont, U.S. Pat. No. 5,865,823 issued on Feb. 2, 1999 in the name of Curro, and U.S. Pat. No. 5,571,096 issued to Dobrin et al. on Nov. 5, 1996. Each of these references is hereby incorporated by reference herein.

The backsheet 202, or any portion thereof, may be elastically extensible in one or more directions. In one embodiment, the backsheet 202 may comprise a structural elastic like film ("SELF") web as described in U.S. Pat. No. 5,518,801, which issued to Chappell, et, al. on May 21, 1996, which is incorporated herein by reference. In alternate embodiments, the backsheet 202 may comprise elastomeric films, foams, strands, or combinations of these or other suitable materials with nonwovens or synthetic films.

The size of the backsheet 202 is dictated by the size of the absorbent core 206 and the exact diaper design selected. In a preferred embodiment, the backsheet 202 has a modified hourglass-shape extending beyond the absorbent core 206 a minimum distance of at least about 1.3 centimeters to about 2.5 centimeters (about 0.5 to about 1.0 inch) around the entire diaper periphery.

The topsheet 204 comprises the apertured formed film web of the present invention as is described above so as to provide the comfort and fluid handling benefits of the present invention. Preferably, the topsheet 204 is sized to coincide with the backsheet 202.

The topsheet 204 and the backsheet 202 are joined together in any suitable manner. As used herein, the term "joined" encompasses configurations whereby the topsheet 204 is directly joined to the backsheet 202 by affixing the topsheet 204 directly to the backsheet 202, and configurations whereby the topsheet 204 is indirectly joined to the backsheet 202 by affixing the topsheet 204 to intermediate members which in turn are affixed to the backsheet 202. In a preferred embodiment, the topsheet 204 and the backsheet 202 are affixed directly to each other in the diaper periphery by attachment means (not shown) such as an adhesive or any other attachment means as known in the art. For example, a uniform continuous layer of adhesive, a patterned layer of adhesive, or an array of separate lines or spots of adhesive can be used to affix the topsheet 204 to the backsheet 202.

Tape tab fasteners (not shown for clarity) are typically applied to the back waistband region of the diaper 202 to provide a fastening means for holding the diaper on the wearer. The tape tab fasteners can be any of those well known in the art, such as the fastening tape disclosed in U.S. Pat. No. 3,848,594 (Buell), issued Nov. 19, 1974, the disclosure of which is hereby incorporated by reference. These tape tab fasteners or other diaper fastening means are typically applied near the corners of the diaper 200.

Elastic members (also not shown for clarity) are disposed adjacent the periphery of the diaper 200, preferably along each longitudinal edge 203, so that the elastic members tend to draw and hold the diaper 200 against the legs of the wearer. Alternatively, the elastic members can be disposed adjacent either or both of the end edges 201 of the diaper 200 to provide a waistband as well as or rather than leg cuffs. For example, a suitable waistband is disclosed in U.S. Pat. No. 4,515,595 (Kievit et al), issued May 7, 1985, the disclosure of which is hereby incorporated by reference. In addition, a method and apparatus suitable for manufacturing a disposable diaper having elastically contractible elastic members is described in U.S. Pat. 4,081,301 (Buell), issued Mar. 28, 1978, the disclosure of which is hereby incorporated herein by reference.

The elastic members are secured to the diaper 200 in an elastically contractible condition so that in a normally unrestrained configuration, the elastic members effectively contract or gather the diaper 200. The elastic members can be secured in an elastically contractible condition in at least two ways. For example, the elastic members can be stretched and secured while the diaper 200 is in an uncontracted condition. Alternatively, the diaper 200 can be contracted, for example, by pleating, and the elastic members secured and connected to the diaper 200 while the elastic members are in their unrelaxed or unstretched condition. The elastic members may extend along a portion of the length of the diaper 200. Alternatively, the elastic members can extend the entire length of the diaper 200, or any other length suitable to provide an elastically contractible line. The length of the elastic members is dictated by the diaper design.

The elastic members can be in a multitude of configurations. For example, the width of the elastic members can be varied from about 0.25 millimeters (0.01 inches) to about 25 millimeters (1.0 inch) or more; the elastic members can comprise a single strand of elastic material or can comprise several parallel or non-parallel strands of elastic material; or the elastic members can be rectangular or curvilinear. Still further, the elastic members can be affixed to the diaper in any of several ways which are known in the art. For example, the elastic members can be ultrasonically bonded, heat and pressure sealed into the diaper 200 using a variety of bonding patterns or the elastic members can simply be glued to the diaper 200.

The absorbent core 206 of the diaper 200 is positioned between the topsheet 204 and the backsheet 202. The absorbent core 206 can be manufactured in a wide variety of sizes and shapes (e.g., rectangular, hourglass, asymmetrical, etc.). The total absorbent capacity of the absorbent core 206 should, however, be compatible with the design liquid loading for the intended use of the absorbent article or diaper. Further, the size and absorbent capacity of the absorbent core 206 can vary to accommodate wearers ranging from infants through adults.

As shown in FIG. 13, the absorbent core 206 includes a fluid storage/distribution member 208. In a preferred configuration such as depicted in FIG. 13, the absorbent core 206 preferably further includes an acquisition layer or member 210 in fluid communication with the fluid storage/distribution member 208 and located between the fluid storage/distribution member 208 and the topsheet 204. The acquisition layer or member 210 may be comprised of several different materials including nonwoven or woven polymeric films of synthetic fibers including polyester, polypropylene, or polyethylene, natural fibers including cotton or cellulose, blends of such fibers, or any equivalent materials or combinations of materials.

In use, the diaper 200 is applied to a wearer by positioning the back waistband region under the wearer's back, and drawing the reminder of the diaper 200 between the wearer's legs so that the front waistband region is positioned across the front of the wearer. The tape-tab or other fasteners are then secured preferably to outwardly facing areas of the diaper 200.

EXAMPLE

This example demonstrates the extrusion and aperturing of an apertured web comprising a three layer polymeric film having permanent hydrophilicity according to the present invention.

Extrusion Apparatus

A typical extrusion apparatus for a three layer film uses three extruders, a fixed plate feedblock, a single manifold flat die, and a cast film line. A description of each piece of equipment used to make film samples is provided below:
Extruders:
Two sizes of extruders were used. The thick hydrophobic layer was extruded by a 1 1/4 inch diameter, 30 L/D ("length to diameter ratio), extruder while the thinner hydrophilic and tie layers were extruded by 1 inch diameter, 24 L/D, extruders. A general purpose screw was used in all extruders having 8 sections of feed, 8 sections of transition, 8 sections of metering and a compression ratio of 2 1/2 to 1.
Adapting Piping:
The piping that connected the extruders to the feedblock was less than 24" in length. The piping temperatures were maintained at the same temperatures as the metering zone of each respective extruder.
Feedblock:
The feedblock was a one temperature zone, fixed plate block. The distribution plate was machined for 80/10/10 % layering. The 80% outer layer was oriented toward the chill roll.
Die:
A 14 inch (35 cm) coathanger die with a flex-lip die gap was used. A suitable die is available from Killion Extruders of Cedar Grove, N.J.
Cast Film Line:
A 12 to 16 inch wide cast film line with surface speeds up to 100 feet per minute was used. The chill roll is typically cooled by city water at temperatures between 45 and 75° F. (7–24° C.) and the film edge was fixed by edge pinning. Typical surface speeds are 50 to 70 fpm to produce a 1.0 mil (25μ) film.

Materials

Hytrel Resins:
Hytrel® HTR 8171 and Hytrel® HTR 8206 from E. I DuPont of Wilmington, Del.
Tie Layer:
Bynel 3860 from DuPont
Polyethylene:
X-8318 resin from Tredegar Film Products of Richmond, Va.

Processing of Materials

Material Preparation:
Hytrel resins were either dried overnight at 175° F. (79° C.) in a dehumidifying drier (or for material recently received from the manufacturer dried at 230° F. (110° C.) for 2 to 4 hours). Then a blend of Hytrel® HTR 8171 and Hytrela HTR 8206 was physically blended or tumbled immediately prior to feeding the extruder hopper. Polyethylene and Bynel tie layer resins were used directly from their containers without drying or other special handling.

Extrusion Condition

Coextrusions were run at the following temperatures. The temperatures were selected to minimize edge encapsulation.

| Material | Zone Temperature (° F./° C.) | | |
| --- | --- | --- | --- |
|  | Feed | Plasticizing | Meter |
| Hytrel | 320/160 | 350/177 | 380/193 |
| Tie Layer | 250/120 | 390199 | 400/204 |
| PE | 350/177 | 400/204 | 440/227 |
| Feedblock/Die | 420/216 | | |

A coextruded three layer film having a hydrophilic layer comprising equal parts of Hytrele® HTR 8171 and Hytrele HTR 8206, a tie layer comprising Bynel 3860, and an opacified polyethylene layer was extruded using the apparatus described above and the following specific setup parameters to form a 1 mil (25µ) film.

|  | Hytrel Extruder | Tie Layer Extruder | PE Extruder |
| --- | --- | --- | --- |
| Screw Diameter (in/mm.) | 1/25 | 1/25 | 1¼/31 |
| Screw Speed (rpm) | 10.5 | 11.5 | 77 |
| Pressure (psi) | 1050 | 1375 | 3240 |

The resulting film has a Hytrel/tie layer/polyethylene layer weight ratio of 10/10/80 and a thickness of 1 mil (25µ).

Film Aperturing

The extruded trilayer film comprising a polyethylene layer, a Bynel® 3860 layer and a 50/50 Hytrel® HTR 8171/Hytrel® HTR 8206 layer (80/10/10 layer weight ratio) described above was hydroformed in accordance with the method described in U.S. Pat. No. 4,629,643 to Curro to provide a plurality of female macroapertures with microapertures oriented in the opposite direction. The film is soft to the touch and has good fluid handling properties.

Analytical Methods

The following are representative analytical methods which have been found suitable for and useful in determining the performance of fluid transport polymeric films in accordance with the present invention.

1. Water Contact Angle The contact angle formed between the solid surface of an unapertured film and the meniscus of a water drop is a measure of solid substrate hydrophilicity/hydrophobicity. The lower the water contact angle, the higher the substrate hydrophilicity. The method described below is used for water contact angle measurement and more specifically used to define degree of hydrophilicity or hydrophobicity in accordance with the present invention.

A model NRL Goniometer (Rame-Hart, Inc., Mountain Lake, N.J.) may be used to as measure water contact angle. The water contact angle is typically measured in a room held at a temperature of 73° F. (23° C.)and a 50% relative humidity. A 4 µL droplet of deionized water is placed on a flat film (i.e., unapertured) sample sitting on the goiniometer platform to measure contact angle at room temperature.

The goiniometer is calibrated according to the following procedure:

1. Level the instrument using a bubble level to ensure that the sample platform is level.

2. Adjust the instrument light such that the droplet is clearly visible.

3. Place a 4 µL droplet of deionized water on a ⅜ in. thick piece of Lexan.®. (available from General Electric) which has been previously washed with methanol and allowed to dry completely.

4. Measure the contact angle of the drop. The instrument is properly calibrated if the contact angle of water on Lexan fills within the range of 68±3 degrees.

Sample measurements are obtained according to the following procedure: 1. A representative sample is cut from an unapertured film, the sample having dimensions of approximately 2.5 cm×5 cm. 2. The sample is placed on the sample platform. Double sided adhesive tape is used, to secure the sample on the platform and keep the sample flat. 3. A 4 µ.L droplet of deionized water is placed onto the sample. 4. The position of the platform is adjusted (vertically and horizontally and focused to get a clear view of the droplet. 5. The contact angle is measured and recorded after the water droplet has been on the sample for 3 minutes, to ensure equilibration of the sample. 6. Steps 1–5 are repeated 3 times for each sample tested. 7. The average contact angle for each sample is calculated.

The disclosures of all patents, patent applications (and any patents which issue thereon, as well as any corresponding published foreign patent applications), and publications mentioned throughout this description are hereby incorporated by reference herein. It is expressly not admitted, however, that any of the documents incorporated by reference herein teach or disclose the present invention.

While various embodiments and/or individual features of the present invention have been illustrated and described, it would be obvious to those skilled in the art that various other changes and modifications can be made without departing from the spirit and scope of the invention. As will be also be apparent to the skilled practitioner, all combinations of the embodiments and features taught in the foregoing disclosure are possible and can result in preferred executions of the invention. It is therefore intended to cover in the appended claims all such changes and modifications that are within the scope of this invention.

What is claimed is:

1. An apertured formed film web having a first surface and a second surface that is suitable for use as a topsheet on an absorbent article, said web comprising:

a first layer; and a second layer;

wherein one of said first layer and said second layer comprises a hydrophilic block copolymer of a polyether and another polymer selected from the group consisting of a polyester, a polyamide, and a polyurethane and the other of said first and second layers comprises a polymeric hydrophobic layer; and said formed film web contains a plurality of micro- and macro-apertures having said hydrophilic block copolymers on inside surfaces of said apertures and said apertures form a plurality of fluid passageways placing said first and second surfaces in fluid communication with one another.

2. The apertured formed film web of claim 1, wherein said first layer comprises a hydrophilic block copolymer of a polyether and another polymer selected from the group consisting of a polyester, a polyamide, and a polyurethane and said second layer is hydrophobic.

3. The apertured formed film web of claim 1, wherein said first layer is hydrophobic and said second layer comprises a hydrophilic block copolymer of a polyether and another polymer selected from the group consisting of a polyester, a polyamide, and a polyurethane.

4. The apertured formed film web of claim 3, wherein said apertured formed film web further comprises at least one intermediate layer.

5. The apertured formed film web of claim 4, wherein said intermediate layer is a tie layer comprising a polymeric material that is able to bond with both of said first and second layers using bonding means selected from the group consisting of chemical bonds, physical entanglement of polymeric chains, and combinations of chemical bonding and physical entanglement.

6. The apertured formed film web of claim 5, wherein said tie layer comprises a polymer comprising a monomer selected from the group consisting of anhydride modified ethylene methyl acrylate, anhydride modified ethylene vinyl acetate, anhydride modified polyolefins, and mixtures thereof.

7. The apertured formed film web of claim 4, wherein said apertured formed film web comprises three intermediate layers.

8. The apertured formed film web of claim 1, wherein the contact angle of water on said hydrophilic layer is less than about 30 degrees.

9. The apertured formed film web of claim 1, wherein the contact angle of water on said hydrophobic layer is greater than about 80 degrees.

10. The apertured formed film web of claim 1, wherein said hydrophobic layer comprises a mixture of polyethylene resins.

11. The apertured formed film web of claim 1, wherein said apertures have a female configuration with respect to said first surface.

12. The apertured formed film web of claim 1, wherein said apertures have a male configuration with respect to said first surface.

13. The apertured formed film web of claim 1, wherein said macroapertures have a female configuration with respect to said first surface.

14. The apertured formed film web of claim 13, wherein said microapertures are formed first followed by formation of said macroapertures and said macroapertures are formed in the same direction as said microapertures were formed.

15. The apertured formed film web of claim 13, herein said microapertures are formed first followed by formation of said macroapertures and said macroapertures are formed in the opposite direction as said microapertures were formed.

16. The apertured formed film web of claim 1, wherein said macroapertures have a male configuration with respect to said first layer.

17. The apertured formed film web of claim 16, wherein said microapertures are formed first followed by formation of said macroapertures and said macroapertures are formed in the same direction as said microapertures were formed.

18. The apertured formed film web of claim 16, wherein said microapertures are formed first followed by formation of said macroapertures and said macroapertures are formed in the opposite direction as said microapertures were formed.

19. The apertured formed film web of claim 2, wherein said first surface is provided with microscopic spaced apart depositions of a material having a surface energy that is lower than the surface energy of said first layer.

20. The apertured formed film web of claim 19, wherein said low surface energy material comprises a silicone resin.

21. The apertured formed film web of claim 1, wherein said formed film web comprises a dual layer structure and first layer comprises a hydrophobic polyester and said second layer comprises a hydrophilic block copolymer of a polyether and a polyester.

22. An apertured formed film web having a first surface and a second surface that is suitable for use as a topsheet on an absorbent article, said web comprising:
    a first layer, said first layer comprising polyethylene;
    a second layer, said second layer comprising a hydrophilic block copolymer of a polyether; and
    at a tie layer located between said first layer and said second layer;
wherein said formed film web contains a plurality of micro- and macro-apertures having said hydrophilic block copolymers on inside surfaces of said apertures and said apertures form a plurality of fluid passageways placing said first and second surfaces in fluid communication with one another.

23. An absorbent article comprising,
    (a) a topsheet comprising:
        a first layer;
        a second layer; and
        at least one intermediate layer located between said first layer and said second layer;
        wherein one of said first layer and said second layer comprises a hydrophilic block copolymer of a polyether and another polymer selected from the group consisting of a polyester, a polyamide, and a polyurethane and the other of said first and second layers comprises a polymeric hydrophobic layer; and said formed film web contains a plurality of micro- and macro-apertures having said hydrophilic block copolymers on inside surfaces of said apertures and said apertures form a plurality of fluid passageways placing said first and second surfaces in fluid communication with one another;
    (b) a backsheet; and
    (c) an absorbent structure disposed between said topsheet and said backsheet.

24. The absorbent article of claim 23, wherein said first layer is hydrophobic and said second layer comprises a hydrophilic block copolymer of a polyether and another polymer selected from the group consisting of a polyester, a polyamide, and a polyurethane.

25. The absorbent article of claim 23, wherein said apertured formed film web comprises one intermediate layer and said intermediate layer comprises a polymer comprising a monomer selected from the group consisting of anhydride modified ethylene methyl acrylate, anhydride modified ethylene vinyl acetate, and mixtures thereof.

26. The absorbent article of claim 23, wherein said macroapertures have a female configuration with respect to said first surface, said microapertures are formed first followed by formation of said macroapertures, and said macroapertures are formed in the opposite direction as said microapertures were formed.

27. The absorbent article of claim 23, wherein said first surface is provided with microscopic spaced apart depositions of a material having a surface energy that is lower than the surface energy of said first layer.

28. The absorbent article of claim 23, wherein said absorbent article is a diaper.

29. The absorbent article of claim 23, wherein said absorbent article is a catamenial pad.

30. An apertured formed film web having a first surface and a second surface that is suitable for use as a topsheet on an absorbent article, said web comprising:
    a first layer; and
    a second layer;

wherein each of said first layer and said second layer comprises a hydrophilic block copolymer of a polyether and another polymer selected from the group consisting of a polyester, a polyamide, and a polyurethane and said formed film web contains a plurality of micro- and macro-apertures having said hydrophilic block copolymers on inside surfaces of said apertures and said apertures form a plurality of fluid passageways placing said first and second surfaces in fluid communication with one another.

31. The apertured formed film web of claim 30, wherein said apertured formed film web further comprises at least one intermediate layer.

32. The apertured formed film web of claim 31, wherein said intermediate layer is a tie layer comprising a polymeric material that is able to bond with both of said first and second layers using bonding means selected from the group consisting of chemical bonds, physical entanglement of polymeric chains, and combinations of chemical bonding and physical entanglement.

33. The apertured formed film web of claim 32, wherein said tie layer comprises a polymer comprising a monomer selected from the group consisting of anhydride modified ethylene methyl acrylate, anhydride modified ethylene vinyl acetate, anhydride modified polyolefins, and mixtures thereof.

34. The apertured formed film web of claim 31, wherein said apertured formed film web comprises three intermediate layers.

35. The apertured formed film web of claim 34, wherein said three intermediate layers comprise a hydrophobic layer disposed between two tie layers.

36. The apertured formed film web of claim 35, wherein said hydrophobic layer is polyethylene and said tie layers comprise a polymer comprising a monomer selected from the group consisting of anhydride modified ethylene methyl acrylate, anhydride modified ethylene vinyl acetate, anhydride modified polyolefins, and mixtures thereof.

37. The apertured formed film web of claim 30, wherein said first surface is provided with microscopic spaced apart depositions of a material having a surface energy that is lower than the surface energy of said first layer.

38. The apertured formed film web of claim 37, wherein said low surface energy material comprises a silicone resin.

* * * * *

UNITED STATES PATENT AND TRADEMARK OFFICE
CERTIFICATE OF CORRECTION

PATENT NO. : 6,461,716 B1
DATED : October 8, 2002
INVENTOR(S) : Lee et al.

It is certified that error appears in the above-identified patent and that said Letters Patent is hereby corrected as shown below:

Column 1,
Line 62, delete "inter fiber" and insert therefor -- inter-fiber --.

Column 5,
Line 22, please move "(1)" to the beginning of the line.
Line 40, after "43" please delete "." (the period) and insert therefor -- , -- (a comma).

Column 6,
Line 18, please move "(2)" to the beginning of the line.
Line 67, please delete "12inches" and insert therefor -- 12 inches --.

Column 7,
Lines 11, 16 and 20, please delete "12inches" and insert therefor -- 12 inches --.

Column 13,
Line 8, please delete "*Teleology*" and insert therefor -- *Technology* --.

Column 14,
Line 32, please delete "80110/10" and insert therefor -- 80/10/10 --.

Column 18,
Line 40, please move "(3)" to the beginning of the line.
Line 52, please move "(4)" to the beginning of the line.
Line 55, please move "(5)" to the beginning of the line.
Line 65, please move "Chatteijee" and insert therefor -- Chatterjee --.

Column 22,
Line 26, please delete "liquid absor-" and insert therefor -- liquid-absor- --.

Column 24,
Line 50, please delete "preferred" and insert therefor -- preferred --.
Line 59, please delete "emcom-" and insert therefor -- encom- --.
Line 64, please delete "poly propylene" and insert therefor -- polypropylene --.
Line 67, please delete "Exaamples" and insert therefor -- Examples --.

Column 25,
Line 2, please delete "4,959,264 issue" and insert therefor -- 4,950,264 issued --.
Line 9, please delete "above-reference" and insert therefor -- above-referenced --.

UNITED STATES PATENT AND TRADEMARK OFFICE
CERTIFICATE OF CORRECTION

PATENT NO. : 6,461,716 B1
DATED : October 8, 2002
INVENTOR(S) : Lee et al.

It is certified that error appears in the above-identified patent and that said Letters Patent is hereby corrected as shown below:

Column 26,
Line 23, please delete "elastic like" and insert therefor -- elastic-like --.

Column 28,
Line 20, please delete "$^1$ ¼" and insert therefor -- 1 ¼ --.
Line 26, please delete "$^2$ ½" and insert therefor -- 2 ½ --.
Line 64, please delete "Hytrela" and insert therefor -- Hytrel® --.

Column 29,
Line 1, please delete "Condition" and insert therefor -- Conditions --.
Line 16, please delete "Hytrele®" and insert therefor -- Hytrel® --.
Line 16, please delete "Hytrele" and insert therefor -- Hytrel® --.
Line 58, please delete "as"

Column 30,
Line 11, before "1." please insert carriage return.
Line 13, before "2." please insert carriage return.
Line 15, before "3." please insert carriage return.
Line 16, before "4." please insert carriage return.
Line 18, before "5." please insert carriage return.
Line 21, before "6." please insert carriage return.
Line 22, before "7." please insert carriage return.

Column 31,
Line 42, please delete "herein" and insert therefor -- wherein --.

Signed and Sealed this

Twenty-ninth Day of June, 2004

JON W. DUDAS
*Acting Director of the United States Patent and Trademark Office*